(12) United States Patent
Thirring et al.

(10) Patent No.: US 7,816,389 B2
(45) Date of Patent: Oct. 19, 2010

(54) ORGANIC COMPOUNDS

(75) Inventors: Klaus Thirring, Vienna (AT); Gerd Ascher, Kundl (AT); Susanne Paukner, Vienna (AT); Werner Heilmayer, Zillingtal (AT); Rodger Novak, Vienna (AT)

(73) Assignee: Nabriva Therapeutics Forschungs GmbH, Vienna (AT)

( * ) Notice: Subject to any disclaimer, the term of this patent is extended or adjusted under 35 U.S.C. 154(b) by 0 days.

(21) Appl. No.: 11/814,673

(22) PCT Filed: Jan. 11, 2007

(86) PCT No.: PCT/AT2007/000009

§ 371 (c)(1),
(2), (4) Date: Nov. 15, 2007

(87) PCT Pub. No.: WO2007/079515

PCT Pub. Date: Jul. 19, 2007

(65) Prior Publication Data

US 2008/0287442 A1    Nov. 20, 2008

(30) Foreign Application Priority Data

Jan. 16, 2006    (EP) ................... 06000827

(51) Int. Cl.
*A61K 31/40* (2006.01)
*A61K 31/341* (2006.01)
*A61K 31/4174* (2006.01)
*A61K 31/495* (2006.01)
*A61K 31/5375* (2006.01)
*C07D 233/66* (2006.01)
*C07D 207/34* (2006.01)
*C07D 211/36* (2006.01)
*C07D 265/30* (2006.01)
*C07D 307/56* (2006.01)

(52) U.S. Cl. ............ 514/398; 544/106; 544/358; 546/290; 546/304; 548/316.4; 548/326.5; 548/541; 548/557; 549/475; 549/480; 514/231.2; 514/255.01; 514/255.02; 514/344; 514/352; 514/424; 514/426; 514/471; 514/473; 514/511; 560/147

(58) Field of Classification Search ............ 514/511, 514/231.02, 255.01, 255.02, 344, 352, 398, 514/424, 426, 471, 473; 560/147; 546/290, 546/304; 548/316.4, 326.5, 541, 557; 544/358; 549/106, 475, 480
See application file for complete search history.

(56) References Cited

U.S. PATENT DOCUMENTS

| 6,753,445 | B2  | 6/2004  | Ascher et al. |
| 7,169,804 | B2* | 1/2007  | Ascher et al. ............ 514/423 |
| 7,569,587 | B2  | 8/2009  | Ascher et al. |
| 2005/0131023 | A1 | 6/2005 | Ascher et al. |
| 2005/0215637 | A1 | 9/2005 | Ascher et al. |
| 2005/0250811 | A1 | 11/2005 | Berner et al. |
| 2007/0270404 | A1 | 11/2007 | Ascher et al. |
| 2008/0287442 | A1 | 11/2008 | Thirring et al. |
| 2008/0306072 | A1 | 12/2008 | Mang et al. |
| 2009/0118366 | A1 | 5/2009 | Mang et al. |

FOREIGN PATENT DOCUMENTS

| EP | 0 013 768 A1 | 8/1980 |
| EP | 1 231 915 B1 | 2/2005 |
| WO | WO 01/09095 A1 | 2/2001 |
| WO | WO 2004/089886 A1 | 10/2004 |
| WO | WO 2007/000001 A2 | 1/2007 |
| WO | WO 2007/000004 A1 | 1/2007 |

OTHER PUBLICATIONS

Krishna, P.S. Murali et al., "Production of rifamycin SV using mutant strains of *Amycolatopsis mediterranei* MTCC17," World Journal of Microbiology & Biotechnology, 1999. vol. 15, pp. 741-743.*
Riedl, K. 1976. Studies on pleuromutilin and some of its derivatives. *The Journal of Antibiotics*, 29(2):132-139.
International Search Report from PCT/AT2007/000009 dated Apr. 13, 2007.
Written Opinion of the International Searching Authority from PCT/AT2007/000009 dated Apr. 13, 2007.

* cited by examiner

*Primary Examiner*—Kamal A Saeed
*Assistant Examiner*—Janet L Coppins
(74) *Attorney, Agent, or Firm*—Knobbe Martens Olson & Bear LLP

(57) ABSTRACT

14-O-[(((C$_{1-6}$)Alkoxy-(C$_{1-6}$)alkyl)-phenylsulfanyl)-acetyl]-mutilins, 14-O-[(((C$_{1-6}$)Mono- or dialkylamino-(C$_{1-6}$)alkyl)-phenylsulfanyl)-acetyl]-mutilins, 14-O-[((Hydroxy-(C$_{1-6}$)-alkyl)-phenylsulfanyl)-acetyl]-mutilins, 14-O-[((Formyl-(C$_{0-5}$)-alkyl)-phenylsulfanyl)-acetyl]-mutilins, 14-O-[((Guanidino-imino-(C$_{1-6}$)alkyl)-phenylsulfanyl)-acetyl]-mutilins, 14-O-[((Ureido-imino-(C$_{1-6}$)alkyl)-phenylsulfanyl)-acetyl]-mutilins, 14-O-[((Thioureido-imino-(C$_{1-6}$)alkyl)-phenylsulfanyl)-acetyl]-mutilins, 14-O-[((Isothioureido-imino-(C$_{1-6}$)alkyl)-phenylsulfanyl)-acetyl]-mutilins and their use as pharmaceuticals.

13 Claims, No Drawings

ORGANIC COMPOUNDS

CROSS REFERENCE TO RELATED APPLICATIONS

This application claims to benefit and priority to and is a U.S. National Phase of PCT International Application Number PCT/AT2007/000009, filed on Jan. 11, 2007, designating the United States of America, which claims priority under U.S.C. §119 to European Application 06000827.3 filed on Jan. 16, 2006. The disclosures of the above-referenced applications are hereby incorporated by this reference in their entirety.

The present invention relates to organic compounds, such as pleuromutilins.

Pleuromutilin, a compound of formula

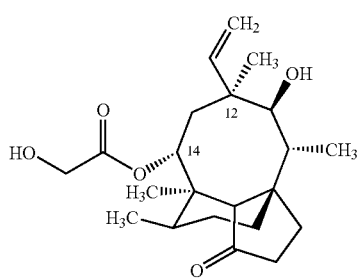

A is a naturally occurring antibiotic, e.g. produced by the basidomycetes *Pleurotus mutilus* and *P. passeckerianus*, see e.g. The Merck Index, 12th edition, item 7694. A number of further pleuromutilins containing the ring structure principle of pleuromutilin and being substituted at the hydroxy group have been developed, e.g. as antimicrobials.

We have now found pleuromutilins with interesting activity.

In one aspect the present invention provides a compound, e.g. a pleuromutilin, selected from the group consisting of 14-O—[(((C$_{1-6}$)Alkoxy-(C$_{1-6}$)alkyl)-phenylsulfanyl)-acetyl]-mutilins, 14-O—[(((C$_{1-6}$)Mono- or dialkylamino-(C$_{1-6}$)alkyl)-phenylsulfanyl)-acetyl]-mutilins, 14-O-[((Hydroxy-(C$_{1-6}$)-alkyl)-phenylsulfanyl)-acetyl]-mutilins, 14-O-[((Formyl-(C$_{0-5}$)-alkyl)-phenylsulfanyl)-acetyl]-mutilins, 14-O-[((Guanidino-imino-(C$_{1-6}$)alkyl)-phenylsulfanyl)-acetyl]-mutilins, 14-O-[((Ureido-imino-(C$_{1-6}$)alkyl)-phenylsulfanyl)-acetyl]-mutilins, 14-O-[((Thioureido-imino-(C$_{1-6}$alkyl)-phenylsulfanyl)-acetyl]-mutilins, 14-O-[((Isothioureido-imino-(C$_{1-6}$)alkyl)-phenylsulfanyl)-acetyl]-mutilins, 14-O-[((Cyano-(C$_{0-5}$)-alkyl)-phenylsulfanyl)-acetyl]-mutilins, 14-O-[((Azido-(C$_{0-5}$)-alkyl)-phenylsulfanyl)-acetyl]-mutilins, 14-O—[(((C$_{1-6}$)Acyloxy-(C$_{1-6}$)alkyl)-phenylsulfanyl)-acetyl]-mutilins, 14-O-[((Benzoyloxy-(C$_{1-6}$)alkyl)-phenylsulfanyl)-acetyl]-mutilins, wherein the phenyl- or 5- or 6-membered heteroaryl-ring is optionally further substituted by up to four groups independently selected from halogen, (C$_{1-6}$)alkyl, aryl, aryl(C$_{1-6}$)-alkyl, (C$_{1-6}$)alkoxy, (C$_{1-6}$)alkoxy(C$_{1-6}$)alkyl, halo(C$_{1-6}$)alkyl, aryl(C$_{1-6}$)alkoxy, hydroxy, nitro, cyano, azido, acyloxy, carbamoyl, mono- or di-N—(C$_{1-6}$)alkylcarbamoyl, (C$_{1-6}$)-alkoxycarbonyl, aryloxycarbonyl, ureido, guanidino, (C$_{1-6}$) alkylguanidino, amidino, (C$_{1-6}$) alkylamidino, sulphonylamino, aminosulphonyl, (C$_{1-6}$)alkylthio, (C$_{1-6}$)-alkylsulphinyl, (C$_{1-6}$) alkylsulphonyl, heterocyclyl, heteroaryl, heterocyclyl(C$_{1-6}$)alkyl and heteroaryl(C$_{1-6}$)alkyl, or two adjacent ring carbon atoms may be linked by a (C$_{3-5}$) alkylene chain, to form a carbocyclic ring.

Preferably, the invention is related to

14-O—[(((C$_{1-6}$)Alkoxy-(C$_{1-6}$)alkyl)-phenylsulfanyl)-acetyl]-mutilins,

14-O—[(((C$_{1-6}$)Mono- or dialkylamino-(C$_{1-6}$)alkyl)-phenylsulfanyl)-acetyl]-mutilins, 14-O—[(((C$_{1-6}$)Acylamino-(C$_{1-6}$)alkyl)-phenylsulfanyl)-acetyl]-mutilins, 14-O-[((Hydroxy-(C$_{1-6}$)-alkyl)-phenylsulfanyl)-acetyl]-mutilins, 14-O-[((Formyl-(C$_{0-5}$)-alkyl)-phenylsulfanyl)-acetyl]-mutilins, 14-O-[((Guanidino-imino-(C$_{1-6}$)alkyl)-phenylsulfanyl)-acetyl]-mutilins.

More preferably, the present invention provides a compound of formula

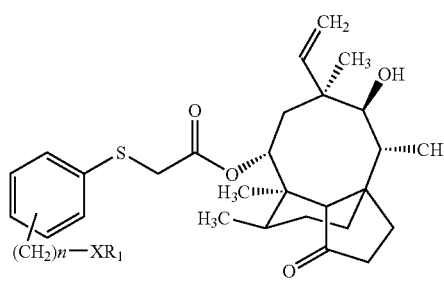

I wherein n is 1 to 6;

X is oxygen, or NR$_2$ wherein R$_2$ is hydrogen or linear or branched (C$_{1-6}$)-alkyl, or hydroxy-(C$_{1-6}$)alkyl or (C$_{1-6}$) alkoxy-(C$_{1-6}$)alkyl, R$_1$ is hydrogen, linear or branched (C$_{1-6}$)-alkyl, mono- or dihalogenated (C$_{1-6}$)-alkyl, amino(C$_{1-6}$)-alkyl, hydroxy (C$_{1-6}$)-alkyl, phenyl(C$_{1-6}$)-alkyl, (C$_{1-6}$)-alkylen, furanyl (C$_{1-6}$)-alkyl, (C$_{3-6}$)-cycloalkyl and the corresponding ammonium salts, e.g. chlorides, or R$_1$ and R$_2$ together with the nitrogen atom to which they are attached form a 5 to 7 membered heterocycle containing at least one nitrogen atom, or XR$_1$ is piperazinyl or morpholinyl.

In another aspect the present invention provides a compound of formula

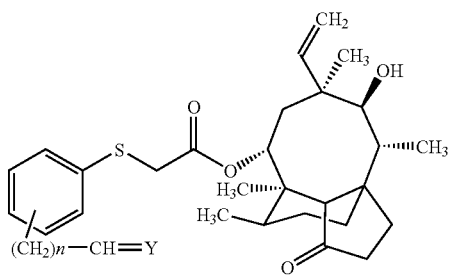

wherein
n is 0 to 5,
Y is oxygen or $NR_3$,
$R_3$ is

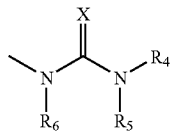

X is oxygen, sulfur, NH or $NR_7$;
or

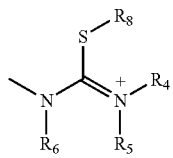

together with a corresponding anion, e.g. chloride,
$R_4$, $R_5$, $R_6$, $R_7$ are hydrogen, linear or branched $C_{1-6}$ alkyl or $C_{3-8}$ cycloalkyl, $R_8$ is $C_{1-4}$ alkyl.
Preferably, the present invention provides a compound of formula II,
wherein
Y is $NR_3$, X is $NR_7$, $R_3$ is

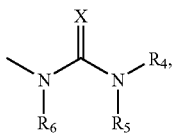

and $R_4$ and $R_7$ together with the nitrogen atoms to which they are attached form a 5 to 7 membered heterocyclic ring containing at least 2 nitrogen atoms, whereas $R_5$ and $R_6$ are as defined above,
or and $R_5$ and $R_6$ together with the nitrogen atoms to which they are attached form a 5 to 7 membered heterocyclic ring containing at least 2 nitrogen atoms, whereas $R_4$ and $R_7$ are as defined above,
or and $R_4$ and $R_5$ together with the nitrogen atoms to which they are attached form a 5 to 7 membered heterocyclic ring containing one or more nitrogen atoms, whereas $R_6$ and $R_7$ are as defined above.

More preferably, the present invention provides a compound of formula II,
wherein
Y is $NR_3$, X is $NR_7$, $R_3$ is

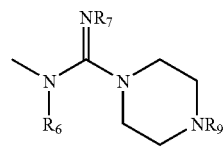

$R_6$ and $R_7$ are as defined above,
$R_9$ is hydrogen, linear or branched $C_{1-6}$ alkyl or acyl, e.g. $C_{1-6}$ acyl.

A pleuromutilin provided by the present invention includes a pleuromutilin having the basic structural elements of the mutilin ring system as set out in formula

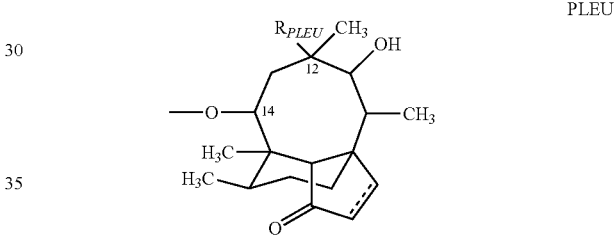

wherein $R_{PLEU}$ is vinyl or ethyl and the dotted line is a bond or is no bond.

The following numbering system is used in the present application:

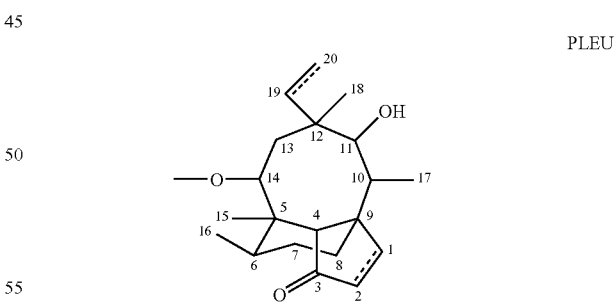

The dotted line between positions 19 an 20 (and between positions 1 and 2) is a bond or is no bond. In a compound of formula A or of formula PLEU a hydrogen atom in positions 4, 7 and/or 8 of the ring system may be replaced by deuterium, and if the dotted line between positions 1 and 2 is no bond (single bond between positions 1 and 2) the ring system may be further substituted in positions 1 and/or 2, e.g. by halogen, deuterium or hydroxy. The group —O— in position 14 is further substituted, preferably by a substituted carbonyl group.

It turned out that the antimicrobial activity against clinical relevant bacterial pathogens (*Staphylococcus aureus, Enterococcus faecalis, Streptococcus pneumoniae, Moraxella catarrhalis* and *Escherichia coli*, see Table 1 hereinafter) of said pleuromutilin-derivatives is particularly enhanced when the phenyl-ring carries a) a saturated or unsaturated carbon atom in meta position in relation to the sulphur bound to the phenyl ring, or b) a saturated or unsaturated carbon atom in ortho position in relation to the sulphur bound to the phenyl ring, provided that the phenyl ring is further substituted by up to four groups as named in claim 1.

Therefore, compounds are preferred, wherein said $(CH_2)_n$-group is in meta position in relation to the sulphur bound to the phenyl-ring. Also preferred are compounds, wherein said $(CH_2)_n$-group is in ortho position in relation to the sulphur bound to the phenyl-ring, with the proviso that the phenyl-ring is further substituted by up to four groups independently selected from halogen, $(C_{1-6})$alkyl, aryl, aryl $(C_{1-6})$-alkyl, $(C_{1-6})$alkoxy, $(C_{1-6})$alkoxy$(C_{1-6})$alkyl, halo $(C_{1-6})$ alkyl, aryl$(C_{1-6})$alkoxy, hydroxy, nitro, cyano, azido, acyloxy, carbamoyl, mono- or di-N—$(C_{1-6})$alkylcarbamoyl, $(C_{1-6})$-alkoxycarbonyl, aryloxycarbonyl, ureido, guanidino, $(C_{1-6})$alkylguanidino, amidino, $(C_{1-6})$ alkylamidino, sulphonylamino, aminosulphonyl, $(C_{1-6})$alkylthio, $(C_{1-6})$-alkylsulphinyl, $(C_{1-6})$ alkylsulphonyl, heterocyclyl, heteroaryl, heterocyclyl$(C_{1-6})$alkyl and heteroaryl$(C_{1-6})$alkyl, or two adjacent ring carbon atoms may be linked by a $(C_{3-5})$ alkylene chain, to form a carbocyclic ring.

In another aspect the present invention provides a compound selected from the group consisting of 14-O-[(3-Hydroxymethyl-phenylsulfanyl)-acetyl]-mutilin, 14-O-[(3-Formyl-phenylsulfanyl)-acetyl]-mutilin, 14-O-[(3-{[(Aminoimino-methyl)-hydrazono]-methyl}-phenylsulfanyl)-acetyl]-mutilin, 14-O-[(3-{[2-(Imino-N-piperazinyl-methyl)-2-methyl-hydrazono]methyl}phenylsulfanyl)-acetyl]-mutilin, 14-O-[(3-[(3-Ethyl-2-methylimino-imidazolidin-1-yl-imino)-methyl]-phenylsulfanyl)-acetyl]-mutilin, 14-O-[(3-{[(Amino-N-piperazinyl-methyl)-hydrazono]-methyl}-phenylsulfanyl)-acetyl]-mutilin, e.g. in the form of a salt, such as a hydrochloride.

In a further aspect the present invention provides a compound selected from the group consisting of 14-O-[(3-Hydroxymethyl-phenylsulfanyl)-acetyl]-mutilin, 14-O-{[3-(Aminoimino-methyl)-hydrazonomethyl-phenylsulfanyl]-acetyl}-mutilin, 14-O-[{3-[((1-Piperazinoiminomethyl)-methylhydrazono)-methyl]-phenylsulfanyl}-acetyl]-mutilin, 14-O-[{3-[(3-Ethyl-(2-ethylimino)-imidazolidin-1-ylimino)-methyl]-phenylsulfanyl}-acetyl]-mutilin, 14-O-[{3-[(1-Piperazinoiminomethyl)-hydrazonomethyl]-phenylsulfanyl}-acetyl]-mutilin, 14-O-[{3-[(2-Morpholin-4-yl-ethoxyimino)-methyl]-phenylsulfanyl}-acetyl]-mutilin, 14-O-[3-{[(2-Pyrrolidin-1-yl-ethoxyimino)-methyl]-phenylsulfanyl}-acetyl]-mutilin, 14-O-[(3-Aminomethyl-phenylsulfanyl)-acetyl]-mutilin, 14-O-[(3-Allylaminomethyl-phenylsulfanyl)-acetyl]-mutilin, 14-O-[3-{[(Furan-2-ylmethyl)-amino]-methyl}-phenylsulfanyl-acetyl]-mutilin, 14-O-[(3-Cyclopropylaminomethyl-phenylsulfanyl)-acetyl]-mutilin, e.g. in the form of a salt, such as a hydrochloride.

A compound provided by the present invention is herein also designated as "compound(s) of (according to) the present invention". A compound of the present invention includes mutilin-14-yl acetic acid esters, e.g. as explicitely defined above, and a compound of formula I or II. A compound of the present invention includes a compound in any form, e.g. in free form, in the form of a salt, in the form of a solvate and in the form of a salt and a solvate.

The compounds of the present invention may be in crystalline or non-crystalline form, and, if crystalline, may optionally be hydrated or a solvate. When some of the compounds of this invention are allowed to crystallise or are recrystallised from organic solvents, solvent of crystallisation may be present in the crystalline product.

This invention includes within its scope such solvates. Similarly, some of the compounds of this invention may be crystallised or recrystallised from solvents containing water. In such cases water of hydration may be present in the crystalline product. This invention includes within its scope stoichiometric hydrates as well as compounds containing variable amounts of water that may be produced by processes such as lyophilisation.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

A salt of a compound of the present invention includes a metal salt or an acid addition salt. Metal salts include for example alkali or earth alkali salts; acid addition salts include salts of a compound of the present invention with an acid, e.g. hydrogen fumaric acid, fumaric acid, naphthalin-1,5-sulphonic acid, hydrochloric acid, deuterochloric acid; preferably hydrochloric acid.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention, if substituted accordingly, may exist in the form of isomers and mixtures thereof; e.g. optical isomers, diastereoisomers, cis/trans conformers, A compound of the present invention may e.g. contain asymmetric carbon atoms and may thus exist in the form of enantiomers or diastereoisomers and mixtures thereof, e.g. racemates. Substituents at any asymmetric carbon atom may be present in the (R)-, (S)- or (R,S)-configuration, preferably in the (R)- or (S)-configuration. E.g., if in a compound of formula I $R_1$ is substituted alkyl and that substituent is attached to a carbon atom of the side chain of such alkyl, the carbon atom to which such substituent is attached is an asymmetric carbon atom and such substitutent may be in the (R)- and (S)-configuration, including mixtures thereof. The configuration of substituents attached to asymmetric carbon atoms of the mutilin-ring is preferably the same as in natural pleuromutilin.

Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of the present invention, where tautomers can exist.

Any compound described herein, e.g. a compound of the present invention and intermediates in their production may be prepared as appropriate, e.g. according, e.g. analogously, to a method as conventional, e.g. or as specified herein.

In another aspect the present invention provides a process for the preparation of 14-O—[((($C_{1-6}$)Alkoxy-($C_{1-6}$)alkyl)-phenylsulfanyl)-acetyl]-mutilins, 14-O—[((($C_{1-6}$)Mono- or dialkylamino-($C_{1-6}$)alkyl)-phenylsulfanyl)-acetyl]-mutilins, 14-O-[((Hydroxy-($C_{1-6}$)-alkyl)-phenylsulfanyl)-acetyl]-mutilins, 14-O-[((Formyl-($C_{0-5}$)-alkyl)-phenylsulfanyl)-acetyl]-mutilins, 14-O-[((Guanidino-imino-($C_{1-6}$) alkyl)-phenylsulfanyl)-acetyl]-mutilins, 14-O-[((Ureido-imino-($C_{1-6}$)alkyl)-phenylsulfanyl)-acetyl]-mutilins, 14-O-[((Thioureido-imino-($C_{1-6}$)alkyl)-phenylsulfanyl)-acetyl]-mutilins, 14-O-[((Isothioureido-imino-($C_{1-6}$)alkyl)-phenylsulfanyl)-acetyl]-mutilins, 14-O—[((($C_{1-6}$)Alkoxy-($C_{1-6}$) alkyl)-5- or 6-membered heteroarylsulfanyl)-acetyl]-mutilins, 14-O-[((Hydroxy-($C_{1-6}$)-alkyl)-5- or 6-membered heteroarylsulfanyl)-acetyl]-mutilins, 14-O-[((Formyl-($C_{0-5}$)-alkyl)-5- or 6-membered heteroarylsulfanyl)-acetyl]-mutilins, 14-O-[((Guanidino-imino-($C_{1-6}$)alkyl)-5- or 6-membered heteroarylsulfanyl)-acetyl]-mutilins, 14-O—[((($C_{1-6}$) Alkylguanidino-imino-($C_{1-6}$)alkyl)-5- or 6-membered heteroarylsulfanyl)-acetyl]-mutilins, 14-O-[((Ureido-imino-($C_{1-6}$)alkyl)-5- or 6-membered heteroarylsulfanyl)-acetyl]-mutilins, 14-O-[((Thioureido-imino-($C_{1-6}$)alkyl)-5- or 6-membered heteroarylsulfanyl)-acetyl]-mutilins, 14-O-[((Isothioureido-imino-($C_{1-6}$)alkyl)-5- or 6-membered heteroarylsulfanyl)-acetyl]-mutilins comprising reacting a a. 14-O-Pleuromutilintosylate with a hydroxy-($C_{1-6}$)-alkyl-thiophenol or 5- or 6-membered hydroxy-($C_{1-6}$)-alkyl-thioheteroaryl compound in the presence of a base (if no further transformation is wanted, the final compounds are isolated and purified in a suitable manner), b1. oxidizing the hydroxy group selectively into a formyl group using an appropriate oxidizing agent (if no further transformation is wanted, the final compounds are isolated and purified in a suitable manner), b2. transforming the hydroxyl group to the corresponding mesylate, c1. condensing the compound bearing the formyl group with a compound having a free amino group c2. Substitution of the mesylate with an azide c2a. Substitution of the mesylate with substituted primary or secondary amines d2. Reduction of the azides to the amines e2. Acylation of the amine.

Compounds having substituents which are intended not to participate in the reaction steps may be used in a protected form. Protecting groups may be removed afterwards without disrupting the remainder of the molecule.

A compound obtained by a process provided by the present invention may be converted into a corresponding salt, according, e.g. analogously, to a method as conventional, e.g. by treatment with an acid, or, metal base, respectively, to obtain an acid addition salt, or, a metal salt, respectively and vice versa, a compound obtained by a process provided by the present invention in the form of a salt, may be converted into the corresponding compound in the form of a free base, according, e.g. analogously, to a method as conventional, e.g. by treatment with an acid if a metal salt is obtained and by treating with a metal base, e.g. a metal hydroxide if an acid addition salt is obtained.

The compounds of the present invention, e.g. including a phenylsulfanyl- or 5-6 membered heteroarylsulfanyl-mutilin provided by the present invention as defined above, and a compound of formula I or II exhibit pharmacological activity and are therefore useful as pharmaceuticals.

For example, the compounds of the present invention show antimicrobial, e.g. antibacterial, activity against gram positive bacteria, such as coagulase-positive and coagulase-negative Staphylococci, e.g. *Staphylococcus aureus, Styphylococcus epidermis, Staphylococcus haemolyticus*, Streptococci, e.g. *Streptococcus pyogenes, Streptococcus pneumoniae, Streptococcus agalacticae*, Enterococci, e.g. *Enterococcus faecium* and Moraxellaceae, e.g. *Moraxella catarrhalis, Pasteurellaceae*, e.g. *Haemophilus influenzae*, as well as against Mycoplasmactaceae, Chlamydiaceae, e.g. *Chlamydia trachomatis, Chlamydia pneumoniae* and obligatory anaerobes, e.g. *Bacteroides fragilis, Clostridium difficile*; in vitro in the Agar Dilution Test or Microdilution Test according to the Climical and Laboratory Standards Institute (CLSI, former National Commitee for Clinical Laboratory Standards (NC-CLS) 2006, Document M7-A7 Vol. 26, No. 2: "Methods for dilution Antimicrobial Susceptibility Tests for Bacteria that Grow Aerobically—Seventh Edition, Approved Standard"; and in the in vitro determination of the antibacterial activity against anaerobic bacteria according to National Committee for Clinical Laboratory Standards (NCCLS) VOL. 24, No. 2, M11-A5, Methods for Antimicrobal Susceptibility Testing of Anaerobic Bacteria; Approved Standard; Sixth Edition (2004) and in vivo in the septicaemic mouse model against *Staphylococcus aureus*.

Compounds of the present invention are therefore suitable for the treatment and prevention of diseases which are mediated by microbes, e.g. by bacteria. Diseases which also may be treated include e.g. diseases mediated by *Helicobacter*, such as *Helicobacter pylori*, and diseases mediated by *Mycobacterium tuberculosis*, diseases mediated by *Legionella pneumophila* or *Neisseriaceae*, diseases which also may be treated include in general inflammatory diseases, where microbes are mediating said inflammation, e.g. including acne.

Compounds of the present invention are preferably useful to treat skin and soft tissue infections, for example epidermal infections like impetigo, bullous impetigo or ecthyma, dermal infections like erysipelas, cellulites, erythrasma or necrotizing fasciitis, follicular infections like folliculitis, furunculosis or carbunculosis, other infections like paronychia, dactylitis, botryomycosis, mastitis, secondarily infected skin lesions, secondarily infected dermatoses, for the decolonization of bacterial carriers, e.g. decolonisation of nasal *Staphylococcus aureus* carriers, and acne, by topical application. Accordingly, in a further aspect the present invention provides the use of a compound of the invention or a pharmaceutically acceptable salt or derivative or solvate thereof in the preparation of a medicament adapted for topical administration for use in the treatment of skin and soft tissue infections and also in the treatment of acne in humans. The invention also provides the use of a compound of the invention, or a pharmaceutical acceptable derivative thereof, in the manufacture of a medicament for use in the treatment of a skin or soft tissue infection.

In another aspect the present invention provides a compound of the present invention for use as a pharmaceutical, preferably as an antimicrobial, such as an antibiotic, e.g. and an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterials, for example diseases mediated by bacteria, e.g. selected from Staphylococci, Streptocooci, Enterococci;

diseases mediated by *Helicobacter*
diseases mediated by *Legionella*, Neisseriaceae, Moraxellaceae, Pasteurellaceae, Corynebacteria,
diseases mediated by *Mycobacterium tuberculosis*,
e.g. diseases mediated by Mycoplasmataceae, Chlamydiaceae and obligatory anaerobes,
for the treatment of acne, and for the decolonization of individuals colonized with bacteria.

In a further aspect the present invention provides a method of treatment of diseases mediated by microbes which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment Includes Treatment and Prophylaxis.

For antimicrobial and acne treatment, the appropriate dosage will, of course, vary depending upon, for example, the chemical nature and the pharmakokinetic data of a compound of the present invention employed, the individual host, the mode of administration and the nature and severity of the conditions being treated. However, in general, for satisfactory results in larger mammals, for example humans, an indicated daily dosage is in the range from about 0.01 to 3 g of a compound of the present invention conveniently administered, for example, in divided doses up to four times a day.

A compound of the present invention may be administered by any conventional route, for example enterally, e.g. including nasal, buccal, rectal, oral, administration; parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of semi-solid formulations, e.g. ointments, creams, gels, pastes, in the form of inhaler powder, foams, tinctures, lip sticks, concealer sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or metal salt; or in free form; optionally in the form of a solvate. A compound of the present invention in the form of a salt exhibit the same order of activity as the compound in free form; optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne or used for the decolonization/sterilisation of bacterial carriers. Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention, e.g. including a compound of formula I, in free form or in the form of a pharmaceutically acceptable salt; e.g. and/or in the form of a solvate; in association with at least one pharmaceutical, excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes.

Unit dosage form may contain, for example, from about 0.01 mg to about 3000 mg, such as 1 mg to about 100 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves; e.g. and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and in the treatment of microbial, e.g. bacterial diseases which comprises administering to a subject in need of such treatment an effective amount of a compound of the present invention, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 4 weeks. Preferred doses in drinking water are from 0.0125 to 0.05 weight by volume, particularly 0.0125 to 0.025, and in foodstuffs from 20 to 400 g/metric ton, preferably 20 to 200 g/metric ton. It is preferred to administer the active compounds of the present invention as a veterinary agent to hens in drinking water, to pigs in foodstuff and to calves orally or parenterally, e.g. in the form of oral or parenteral preparations.

The invention is further described by reference to the following examples. These examples are provided for illustration purposes only and are not intended to be limiting the present invention in any way.

EXAMPLES

Example 1

14-O-[(3-Hydroxymethyl-phenylsulfanyl)-acetyl]-mutilin

Step 1: Pleuromutilintosylate

To a solution of 18.63 g (49.2 mmol) of Pleuromutilin and 9.39 g (49.2 mmol) of toluenesulfonylchloride in 1400 mL of methylethylketone a solution of 4.98 g (49.2 mmol) of triethylamine in 300 mL of methylethylketone is slowly added at ambient temperature. The reaction is stirred for 24 h at ambient temperature, the formed precipitate is filtered off and 2800 mL of water is added to the solution. The solution is extracted three times with ethyl acetate, the organic phase is dried with Na$_2$SO$_4$ and evaporated to dryness under reduced pressure. The crude product is used for the next step without further purification.

$^1$H-NMR (400 MHz, DMSO-d$_6$, δ, ppm, characteristic signals): 0.49 (d, 3H, J=7 Hz, CH$_3$-16); 0.8 (d, 3H, J=7 Hz, CH$_3$-17); 1.02 (s, 3H, CH$_3$-18); 1.29 (s, 3H, CH$_3$-15); 2.38 (bs, 1H, H-4); AB-system (u$_A$=4.75, u$_B$=4.62, J=50 Hz, CH$_2$-22); 5.00 (m, 2H, H-20); 5.52 (d, 1H, J=8 Hz, H-14); 6.04 (dd, 1H, J=11 and 18 Hz, H-19); 7.46 (d, 2H, J=8 Hz, H-24); 7.79 (d, 2H, J=8 Hz, H-23).

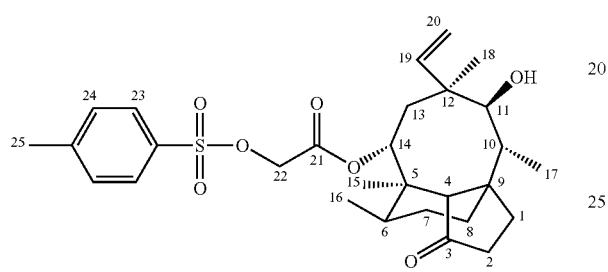

Step 2: 14-O-[(3-Hydroxymethyl-phenylsulfanyl)-acetyl]-mutilin

To 1.96 g (14 mmol) of (3-Mercapto-phenyl)-methanol [prepared from 3-Mercaptobenzoic acid according to: Chemistry Express, Vol 7, No. 11, pp. 865-868 (1992)] in 90 mL of absolute ethanol 322 mg (14 mmol) of sodium is added. After stirring the reaction for 30 min at ambient temperature a solution of 7.45 g (14 mmol) of Pleuromutilintosylate in 130 mL of methylethylketone is added and the reaction stirred at ambient temperature for 16 h. The reaction mixture is evaporated to dryness under reduced pressure, dissolved in ethyl acetate and extracted three times with water. The organic phase is dried with Na$_2$SO$_4$, evaporated to dryness under reduced pressure and the residue is chromatographed on silica gel using dichloromethane/methanol 100:1.5 as mobile phase.

The obtained material was cristalline (Fp. 139-141° C.).

$^1$H-NMR (500 MHz, CDCl$_3$, δ, ppm, characteristic signals): 0.68 (d, 3H, J=7 Hz, CH$_3$-16); 0.88 (d, 3H, J=7 Hz, CH$_3$-17); 1.12 (s, 3H, CH$_3$-18); 1.42 (s, 3H, CH$_3$-15); 2.06 (bs, 1H, H-4); 3.32 (t, 1H, J=6 Hz, H-11); 3.59 (S, 2H, CH$_2$-22); 4.66 (s, 2H, CH$_2$-27); 5.15 and 5.30 (2×m, 2H, H-20); 5.72 (d, 1H, J=8 Hz, H-14); 6.41 (dd, 1H, J=11 and 17 Hz, H-19); 7.19 and 7.28 (2×m, 3H, H-24, 25 and 26); 7.38 (S, 1H, H-23).

$^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.98 (s, 3H, CH$_3$-18); 1.30 (s, 3H, CH$_3$-15); 3.37 (t, 1H, J=6 Hz, H-11); AB-system (u$_A$=3.81, u$_B$=3.74, J=29 Hz, CH$_2$-22); 4.44 (d, 2H, J=6 Hz, CH$_2$-27); 4.95 (m, 2H, H-20); 5.49 (d, 1H, J=8 Hz, H-14), 6.04 (m, 1H, H-19), 7.10-7.27 (4×m, 4H, H-23, 24, 25 and 26).

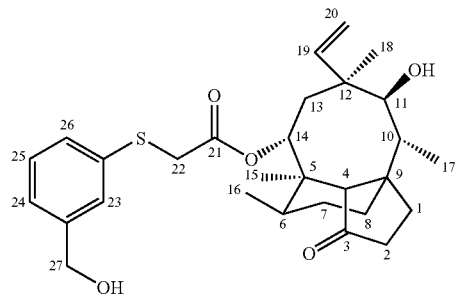

The following compounds are prepared in a similar fashion:

Example 2

Comparison

14-O-[(4-Methyl-phenylsulfanyl)-acetyl]-mutilin $^1$H-NMR (400 MHz, DMSO-d$_6$, δ, ppm, characteristic signals): 0.55 (d, 3H, J=7 Hz, CH$_3$-16); 0.79 (d, 3H, J=7 Hz, CH$_3$-17); 0.98 (s, 3H, CH$_3$-18); 1.30 (s, 3H, CH$_3$-15); 2.24 (s, 3H, CH$_3$-27); 2.35 (bs, 1H, H-4); 3.37 (t, 1H, J=6 Hz, H-11); AB-system (u$_A$=3.75, u$_B$=3.68, J=28 Hz, CH$_2$-22); 4.96 (m, 2H, H-20); 5.48 (d, 1H, J=8 Hz, H-14); 6.03 (dd, 1H, J=11, and 20 Hz, H-19); 7.09 and 7.23 (2×d, 4H, J=8 Hz, arom-H).

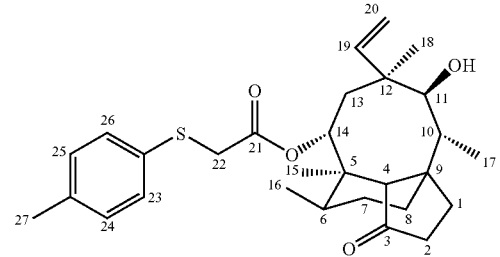

Example 3

14-O-[(5-Hydroxymethyl-2-fluoro-phenylsulfanyl)-acetyl]-mutilin $^1$H-NMR (400 MHz, CD$_3$OD, δ, ppm, characteristic signals): 0.67 (d, 3H, J=7 Hz, CH$_3$-16); 0.89 (d, 3H, J=7 Hz, CH$_3$-17); 1.18 (s, 3H, CH$_3$-18); 1.35 (s, 3H, CH$_3$-15); 2.29 (bs, 1H, H-4); 3.42 (d, 1H, J=7 Hz, H-11); AB-system (u$_A$=3.70, u$_B$=3.60, J=39 Hz, CH$_2$-22); 4.53 (s, 2H, CH$_2$-26); 5.07 (m, 2H, H-20); 5.64 (d, 1H, J=8 Hz, H-14); 6.19 (dd, 1H, J=7 and 19 Hz, H-19); 7.08, 7.27 and 7.44 (3×m, 3H, H-23, 24 and 25).

The required (4-Fluoro-3-mercapto-phenyl)-methanol is prepared in two steps from 3-Chlorosulfonyl-4-fluoro-benzoic acid following the procedure for the preparation of (3-Mercapto-phenyl)-methanol described in Chemistry Express, Vol 7, No. 11, pp. 865-868).

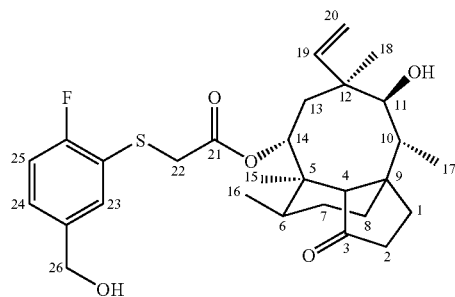

Example 4

14-O-[(2-Hydroxymethyl-4-fluoro-phenylsulfanyl)-acetyl]-mutilin $^1$H-NMR (400 MHz, DMSO-$d_6$, δ, ppm, characteristic signals): 0.51 (d, 3H, J=7 Hz, CH$_3$-16); 0.78 (d, 3H, J=7 Hz, CH$_3$-17); 0.97 (s, 3H, CH$_3$-18); 1.27 (s, 3H, CH$_3$-15); 2.34 (bs, 1H, H-4); 3.37 (d, 1H, J=7 Hz, H-11); AB-system (u$_A$=3.78, u$_B$=3.70, J=29 Hz, CH$_2$-22); 4.56 (d, 2H, J=5 Hz, CH$_2$-26); 4.92 (m, 2H, H-20); 5.45 (d, 1H, J=8 Hz, H-14); 6.19 (dd, 1H, J=11 and 18 Hz, H-19); 7.02 and 7.44 (2×m, 2H, H-24 and 25); 7.20 (m, 1H, H-23).

The required (5-Fluoro-2-mercapto-phenyl)-methanol is prepared from 5-Fluoro-2-mercapto-benzoic acid following the procedure for the preparation of (3-Mercapto-phenyl)-methanol described in Chemistry Express, Vol 7, No. 11, pp. 865-868).

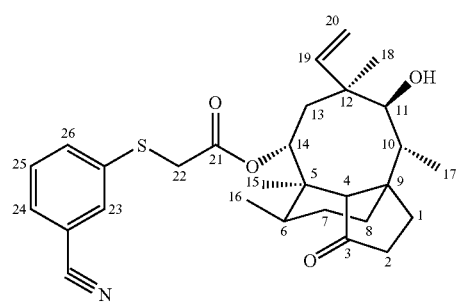

Example 6

14-O-[(4-Hydroxymethyl-phenylsulfanyl)-acetyl]-mutilin $^1$H-NMR (400 MHz, CDCl$_3$, δ, ppm, characteristic signals): 0.68 (d, 3H, J=7 Hz, CH$_3$-16); 0.86 (d, 3H, J=7 Hz, CH$_3$-17); 1.12 (s, 3H, CH$_3$-18); 1.40 (s, 3H, CH$_3$-15); 2.06 (bs, 1H, H-4); 3.32 (dd, 1H, J=7 and 11 Hz, H-11); 3.56 (s, 2H, CH$_2$-22); 4.66 (d, 2H, J=4 Hz, CH$_2$-25); 5.16 and 5.30 (2×m, 2H, H-20); 5.73 (d, 1H, J=8 Hz, H-14); 6.41 (dd, 1H, J=11 and 17 Hz, H-19); 7.28 and 7.38 (2×d, 4H, J=8 Hz, H-23 and 24); 9.91 (s, 1H, 1-25).

The required (4-Mercapto-phenyl)-methanol was prepared from 4-Mercapto-benzoic acid following the procedure for the preparation of (3-Mercapto-phenyl)-methanol described in Chemistry Express, Vol 7, No. 11, pp. 865-868).

Example 5

14-O-[(3-Cyano-phenylsulfanyl)-acetyl]-mutilin $^1$H-NMR (400 MHz, DMSO-$d_6$, δ, ppm, characteristic signals), 0.55 (d, 3H, J=7 Hz, CH$_3$-16); 0.78 (d, 3H, J=7 Hz, CH$_3$-17); 0.97 (s, 3H, CH$_3$-18); 1.28 (s, 3H, CH$_3$-15); 2.35 (bs, 1H, H-4); 3.36 (t, 1H, J=6 Hz, H-11); AB-system (u$_A$=4.00, u$_B$=3.93, J=31 Hz, CH$_2$-22); 4.97 (m, 2H, H-20); 5.48 (d, 1H, J=8 Hz, H-14); 6.01 (dd, 1H, J=11 and 18 Hz, H-19); 7.45-7.86 (3×m, 4H, H-23, 24, 25 and 26).

The required 3-Mercapto-benzonitrile is prepared from 3-Cyano-benzenesulfonyl chloride following the procedure for the preparation of 3-Mercaptobenzoic acid described in Journal of Heterocyclic Chemistry (1982), 19(4), 961-5.

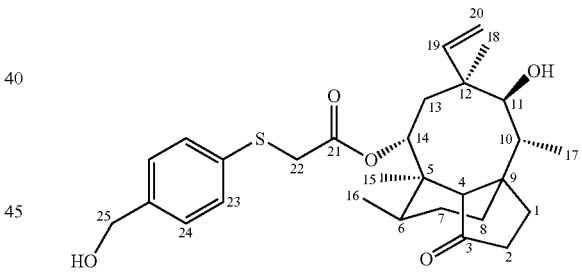

Example 7

14-O-[(2-Hydroxymethyl-phenylsulfanyl)-acetyl]-mutilin $^1$H-NMR (500 MHz, CDCl$_3$, δ, ppm, characteristic signals): 0.60 (d, 3H, J=7 Hz, CH$_3$-16); 0.85 (d, 3H, J=7 Hz, CH$_3$-17); 1.09 (s, 3H, CH$_3$-18); 1.39 (s, 3H, CH$_3$-15); 2.04 (bs, 1H, H-4); 3.30 (t, 1H, J=7 Hz, H-11); AB-system (u$_A$=3.62, u$_B$=3.58, J=21 Hz, CH$_2$-22); AB-system (u$_A$=4.82, u$_B$=4.78, J=19 Hz, CH$_2$-27); 5.12 and 5.28 (2×m, 2H, H-20); 5.67 (d, 1H, J=8 Hz, H-14); 6.35 (dd, 1H, J=11 and 18 Hz, H-19); 7.24 and 7.42 (2×m, 4H, arom-H).

The required (2-Mercapto-phenyl)-methanol is prepared from 2-Mercapto-benzoic acid following the procedure for the preparation of (3-Mercapto-phenyl)-methanol described in Chemistry Express, Vol 7, No. 11, pp. 865-868).

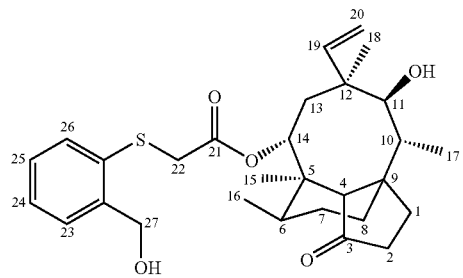

Example 8

14-O-[(2-Hydroxy-6-hydroxymethyl-phenylsulfanyl)-acetyl]-mutilin $^1$H-NMR (400 MHz, DMSO-d$_6$, δ, ppm, characteristic signals): 0.57 (d, 3H, J=7 Hz, CH$_3$-16); 0.79 (d, 3H, J=7 Hz, CH$_3$-17); 0.99 (s, 3H, CH$_3$-18); 1.29 (s, 3H, CH$_3$-15); 2.34 (bs, 1H, H-4); 3.36 (t, 1H. J=6 Hz, H-11); AB-system (u$_A$=3.70, u$_B$=3.59, J=26 Hz, CH$_2$-22); 4.32 (d, 2H, J=5 Hz, CH$_2$-26); 4.95 (m, 2H, H-20); 5.47 (d, 1H, J=8 Hz, H-14); 6.03 (dd, 1H, J=11 and 18 Hz, H-19); 6.75 (d, 1H, J=8 Hz, H-25); 6.98 (dd, 1H, J=2 and 8 Hz, H-24); 7.11 (d, 1H, J=2 Hz, H-23).

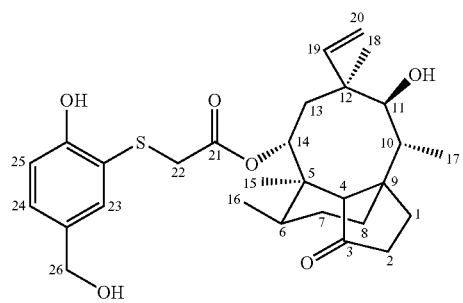

The required 4-Hydroxymethyl-2-mercapto-phenol is prepared from 3-Chlorosulfonyl-4-hydroxy-benzoic acid following the procedure for the preparation of (3-Mercapto-phenyl)-methanol described in Chemistry Express, Vol 7, No. 11, pp. 865-868).

Example 9

14-O-[(3-Formyl-phenylsulfanyl)-acetyl]-mutilin

To 2.38 g (4.75 mmol) of 14-O-[(3-Hydroxymethyl-phenylsulfanyl)-acetyl]-mutilin in 70 mL of dichloromethane is added 2.02 g (4.75 mmol) of Dess-Martin reagent. After stirring the reaction for 60 min at ambient temperature the reaction mixture is filtered, evaporated to dryness under reduced pressure and chromatographed on silica gel using dichloromethane/methanol 100:1 as mobile phase.

$^1$H-NMR (400 MHz, CDCl$_3$, δ, ppm, characteristic signals): 0.68 (d, 3H, J=7 Hz, CH$_3$-16); 0.86 (d, 3H, J=7 Hz, CH$_3$-17); 1.11 (s, 3H, CH$_3$-18); 1.39 (s, 3H, CH$_3$-15); 2.06 (bs, 1H, H-4); 3.32 (m, 1H, H-11), 3.64 (s, 2H, CH$_2$-22); 5.12 and 5.26 (2×m, 2H, H-20); 5.74 (d, 1H, J=8 Hz, H-14); 6.36 and 6.40 (dd, 1H, J=11 and 17 Hz, H-19); 7.45 (t, 1H, J=8 Hz, H-25); 7.62 (m, 1H. H-26); 7.71 (m, 1H, H-24); 7.85 (m, 1H, H-23); 9.97 (s, 1H, H-27).

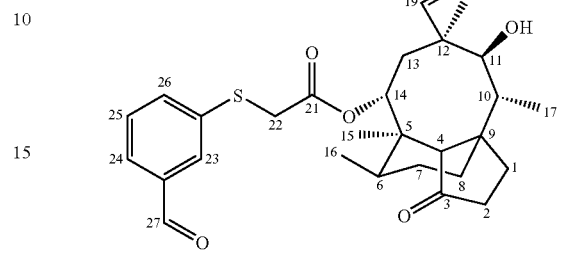

The following compounds are prepared in a similar fashion:

Example 10

14-O-[(2-Formylphenylsulfanyl)-acetyl]-mutilin $^1$H-NMR (400 MHz, DMSO-d$_6$, δ, ppm, characteristic signals): 0.54 (d, 3H, J=7 Hz, CH$_3$-16); 0.79 (d, 3H, J=7 Hz, CH$_3$-17); 0.97 (s, 3H, CH$_3$-18); 1.32 (s, 3H, CH$_3$-15); 2.35 (bs, 1H, H-4); 3.37 (t, 1H, J=6 Hz, H-11); AB-system (u$_A$=3.95, u$_B$=3.88, J=21 Hz, CH$_2$-22); 4.92 (m, 2H, H-20); 5.50 (d, 1H, J=8 Hz, H-14); 6.02 (dd, 1H, J=11 and 18 Hz, H-19); 7.38 and 7.57 (2×t, 2H, J=8 Hz, H-24 and 25); 7.50 and 7.89 (2×d, 2H, J=8 Hz, H-23 and 26); 10.19 (s, 1H. H-27).

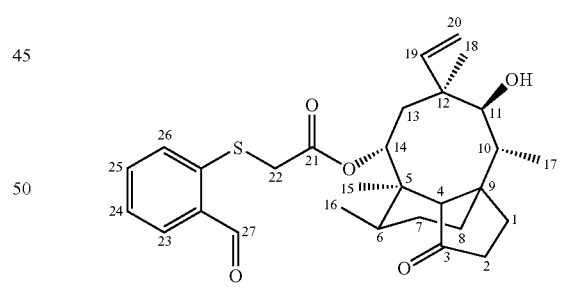

Example 11

14-O-[(4-Formylphenylsulfanyl)-acetyl]-mutilin $^1$H-NMR (500 MHz, DMSO-d$_6$, δ, ppm, characteristic signals): 0.57 (d, 3H, J=7 Hz, CH$_3$-16); 0.78 (d, 3H, J=7 Hz, CH$_3$-17); 0.96 (s, 3H, CH$_3$-18); 1.30 (s, 3H, CH$_3$-15); 2.36 (bs, 1H, H-4); 3.37 (t, 1H, J=6 Hz, H-11); AB-system (u$_A$=4.03, u$_B$=3.98, J=24 Hz, CH$_2$-22); 4.95 (m, 2H, H-20); 5.51 (d, 1H, J=8 Hz, H-14); 6.02 (dd, 1H, J=11 and 18 Hz, H-19); 7.49 and 7.78 (2×d, 4H, J=8 Hz, H-23 and 24); 9.91 (s, 1H, H-25).

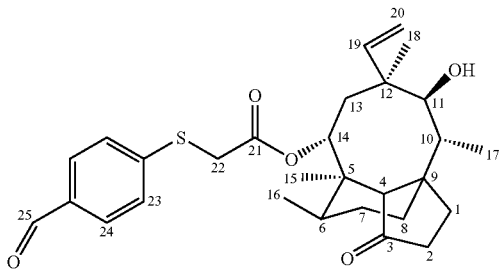

Example 12

14-O-{[3-(Aminoimino-methyl)-hydrazonomethyl-phenylsulfanyl]-acetyl}-mutilin hydrochloride

To 381 mg (0.61 mmol) of 14-O-[(3-Formyl-phenylsulfanyl)-acetyl]-mutilin in 4 mL of N,N-dimethylacetamide is added 83 mg (0.61 mmol) of aminoguanidine-dihydrocarbonate and 0.61 ml of 2N HCl. After stirring the reaction for 12 h at ambient temperature the reaction mixture is evaporated to dryness under reduced pressure and chromatographed on silica gel using dichloromethane/methanol/isopropylether 4:1:1 containing 1% acetic acid as mobile phase.

$^1$H-NMR (400 MHz, DMSO-d$_6$, δ, ppm, characteristic signals): 0.55 (d, 3H, J=7 Hz, CH$_3$-16); 0.78 (d, 3H, J=7 Hz, CH$_3$-17); 0.95 (s, 3H, CH$_3$-18); 1.27 (s, 3H, CH$_3$-15); 2.33 (bs, 1H, H-4); 3.36 (t, 1H, J=6 Hz, H-11); AB-system (u$_A$=3.94, u$_B$=3.85, J=36 Hz, CH$_2$-22); 4.90 (m, 2H, H-20); 5.48 (d, 1H, J=8 Hz, H-14); 6.00 (dd, 1H, J=11 and 18 Hz, H-19); 7.32 (m, 1H, H-25); 7.32 and 7.58 (2×m, 2H, H-24 and 26); 7.83 (s, 1H, H-23); 8.05 (s, 1H, H-27).

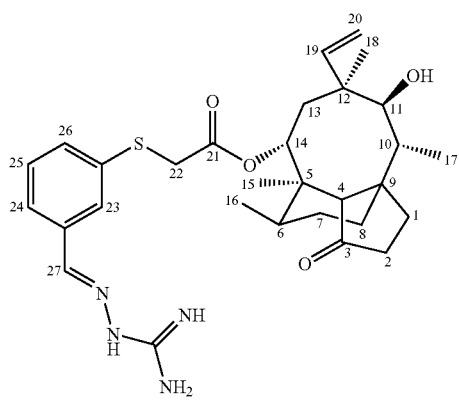

The following compounds were prepared in a similar fashion:

Example 13

14-O-[{3-[((1-Piperazinoiminomethyl)-methylhydrazono)-methyl]-phenylsulfanyl}-acetyl]-mutilin hydrochloride

$^1$H-NMR (500 MHz, CD$_3$OD, δ, ppm, characteristic signals): 0.65 (d, 3H, J=7 Hz, CH$_3$-16); 0.89 (d, 3H, J=7 Hz, CH$_3$-17); 1.03 (s, 3H, CH$_3$-18); 1.37 (s, 3H, CH$_3$-15); 3.34 (s, 3H, N—CH$_3$); 3.41-3.58 (m, 8H, N—(CH$_2$); AB-system (u$_A$=3.78, u$_B$=3.73, J=24 Hz, CH$_2$-22); 5.01 (m, 2H, H-20); 5.64 (d, 1H, J=8 Hz, H-14); 6.15 (dd, 1H, J=11 and 18 Hz, H-19); 7.40, 7.48 and 7.64 (3×m, 3H, H-24, 25 and 26); 7.86 (s, 1H, H-23); 8.14 (bs, 1H, H-27).

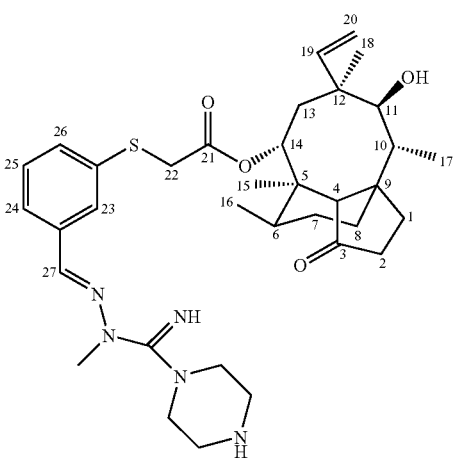

Example 14

14-O-[{3-[(3-Ethyl-2-ethylimino)-imidazolidin-1-ylimino)-methyl]-phenylsulfanyl}-acetyl]-mutilin hydrochloride

$^1$H-NMR (400 MHz, CDCl$_3$, δ, ppm, characteristic signals)-0.66 (d, 3H, J=7 Hz, CH$_3$-16); 0.87 (d, 3H, J=7 Hz, CH$_3$-17); 1.10 (s, 3H, CH$_3$-18); 1.32 (t, 3H, J=7 Hz, CH$_3$-31); 1.39 (s, 3H, CH$_3$-15); 2.06 (bs, 1H, H-4); 3.46 (d, 3H, J=5 Hz, CH$_3$-32); 3.62 (s, 2H, CH$_2$-22); 3.85 and 4.05 (2×m, 4H, CH$_2$-28 and 29); 3.97 (q, 2H, J=7 Hz, CH$_2$-30); 5.12 and 5.25 (2×m, 2H, H-20); 5.70 (d, 1H, J=8 Hz, H-14); 6.37 (dd, 1H, J=11 and 17 Hz, H-19); 7.30-7.55 (3×m, 3H, H-24, 25 and 26); 7.56 (s, 1H, H-23); 7.64 (s, 1H, H-27).

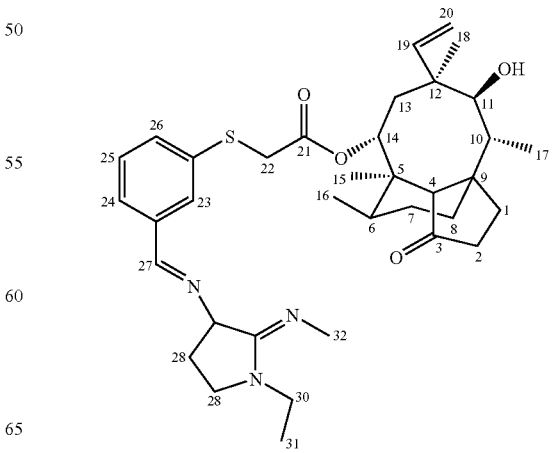

Example 15

14-O-[({3-[(1-Piperazinoiminomethyl)-hydrazonomethyl]-phenylsulfanyl}-acetyl]-mutilin hydrochloride ¹H-NMR (500 MHz, CDCl₃, δ, ppm, characteristic signals): 0.63 (d, 3H, J=7 Hz, CH₃-16); 0.87 (d, 3H, J=7 Hz, CH₃-17); 1.04 (s, 3H, CH₃-18); 1.35 (s, 3H, CH₃-15); 2.25 (bs, 1H, H-4); 3.05 (m, 4H, N—CH₂); 3.64 (m, 6H, N—CH₂, H-22); 5.02 and 5.12 (2×m, 2H, H-20); 5.65 (d, 1H, J=8 Hz, H-14); 6.21 (dd, 1H, J=11 and 17 Hz, H-19); 7.31 (t, 1H, H-25); 7.38 and 7.52 (2×m, 2H, H-24 and 26); 7.77 (bs, 1H, H-23); 8.26 (s, 1H, H-27).

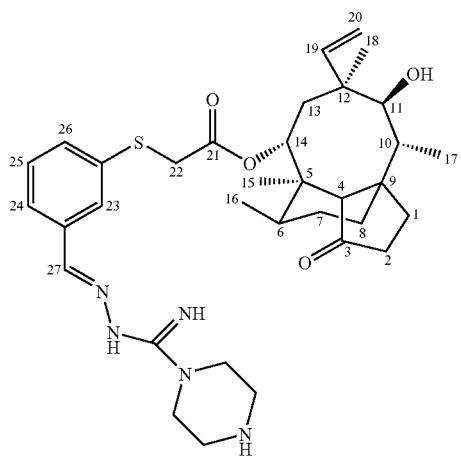

Example 16

14-O-[{3-[(2-Morpholin-4-yl-ethoxyimino)-methyl]-phenylsulfanyl}-acetyl]-mutilin hydrochloride ¹H-NMR (400 MHz, DMSO-d₆, δ, ppm, characteristic signals): 0.55 (d, 3H, J=7 Hz, CH₃-16); 0.78 (d, 3H, J=7 Hz, CH₃-17); 0.95 (s, 3H, CH₃-18); 1.28 (s, 3H, CH₃-15); 2.34 (bs, 1H, H-4); 2.40 (m, 4H, CH₂-30); 2.60 (t, 2H, J=6 Hz, CH₂-29), 3.42 (t, 1H, J=6 Hz, H-11); 3.55 (t, 4H, J=5 Hz, CH₂-31); AB-system (u$_A$=3.88, u$_B$=3.70, J=30 Hz, CH₂-22); 4.21 (t, 2H, J=6 Hz, CH₂-28); 4.90 (m, 2H, H-20); 5.48 (d, 1H, J=8 Hz, H-14); 6.00 (dd, 1H, J=11 and 18 Hz, H-19); 7.30-7.90 (m, 4H, H-23, 24, 25 and 26); 8.17 (s, 1H, H-27).

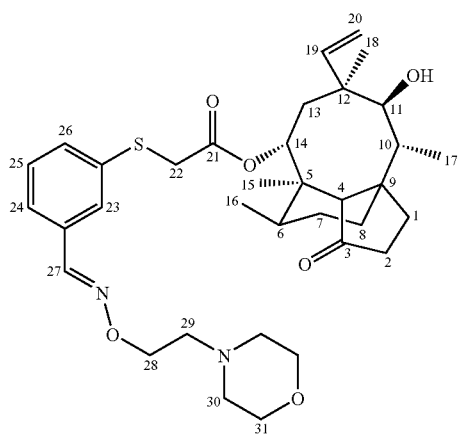

Example 17

14-O-[3-{[(2-Pyrrolidin-1-yl-ethoxyimino)-methyl]-phenylsulfanyl}-acetyl]-mutilin hydrochloride ¹H-NMR (500 MHz, DMSO-d₆, δ, ppm, characteristic signals): 0.55 (d, 3H, J=7 Hz, CH₃-16); 0.78 (d, 3H, J=7 Hz, CH₃-17); 0.96 (s, 3H, CH₃-18); 1.28 (s, 3H, CH₃-15); 2.34 (bs, 1H, H-4); 2.60-3.00 (bm, 10H, CH₂-29, 30 and 31); 3.36 (t, 1H, J=6 Hz, H-11); AB-system (u$_A$=3.88, u$_B$=3.70, J=35 Hz, CH₂-22); 4.26 (t, 2H, J=6 Hz, CH₂-28); 4.90 (m, 2H, H-20); 5.48 (d, 1H, J=8 Hz, H-14); 6.00 (dd, 1H, J=11 and 18 Hz, H-19); 7.30-7.43 (m, 3H, H-24, 25 and 26); 7.58 (s, 1H, H-23); 8.19 (s, 1H, H-27).

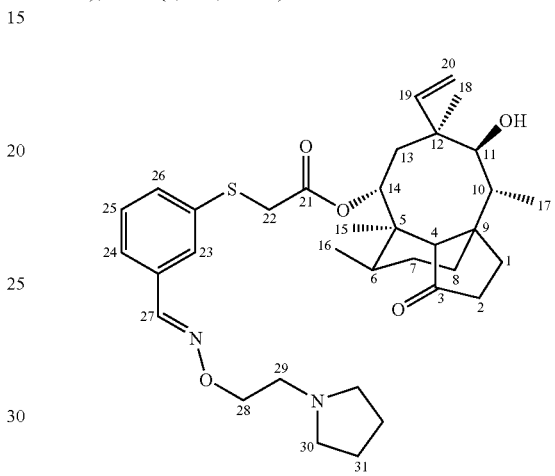

Example 18

14-O-[{4-[(1-Piperazinoiminomethyl)-hydrazonomethyl}-phenylsulfanyl}-acetyl]-mutilin hydrochloride ¹H-NMR (400 MHz, DMSO-d₆, δ, ppm, characteristic signals): 0.51 (d, 3H, J=7 Hz, CH₃-16); 0.77 (d, 3H, J=7 Hz, CH₃-17); 0.97 (s, 3H, CH₃-18); 1.24 (s, 3H, CH₃-15); 2.33 (bs, 1H, H-4); 3.18 (m, 4H, CH₂-29); 3.36 (t, 1H, J=6 Hz, H-11); 3.81 (m, 4H, CH₂-28); AB-system (u$_A$=3.90, u$_B$=3.81, J=34 Hz, CH₂-22); 4.91 (m, 2H, H-20); 5.47 (d, 1H, J=8 Hz, H-14); 6.00 (dd, 1H, J=11 and 18 Hz, H-19); 7.10-7.51 (m, 5H, H-23, 24, 25, 26 and 27).

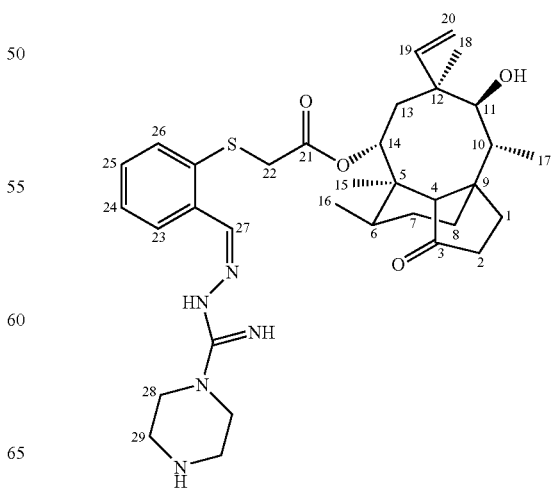

Example 19

14-O-[({2-[(Aminoiminomethyl)-hydrazonomethyl]-phenylsulfanyl}-acetyl]-mutilin hydrochloride

¹H-NMR (400 MHz, DMSO-d$_6$, δ, ppm, characteristic signals): 0.52 (d, 3H, J=7 Hz, CH$_3$-16); 0.75 (d, 3H, J=7 Hz, CH$_3$-17); 0.96 (s, 3H, CH$_3$-18); 1.27 (s, 3H, CH$_3$-15); 2.33 (bs, 1H, H-4); 3.36 (t, 1H, J=6 Hz, H-11); AB-system (u$_A$=3.87, u$_B$=3.781 J=26 Hz, CH$_2$-22); 4.92 (m, 2H, H-20); 5.47 (d, 1H, J=8 Hz, H-14); 5.99 (m, 1H, H-19); 7.25 (m, 2H, H-24 and 25); 7.44 and 7.96 (2×m, 2H, H-23, and 26); 8.54 (s, 1H, H-27).

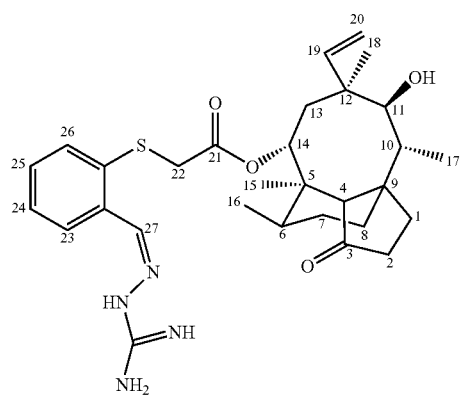

Example 20

14-O-[{4-[(Aminoiminomethyl)-hydrazonomethyl]-phenylsulfanyl}-acetyl]-mutilin hydrochloride

¹H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.97 (s, 3H, CH$_3$-18); 1.30 (s, 3H, CH$_3$-15); 2.36 (bs, 1H, H-4); 3.37 (t, 1H, J=6 Hz, H-11); AB-system (u$_A$=3.94, u$_B$=3.88, J=24 Hz, CH$_2$-22); 4.96 (m, 2H, H-20); 5.50 (d, 1H, J=8 Hz, H-14); 6.03 (dd, 1H, J 11 and 18 Hz, H-19); 7.38 and 7.78 (2×d, 4H, J=8 Hz, H-23 and 24); 8.10 (s, 1H, H-25).

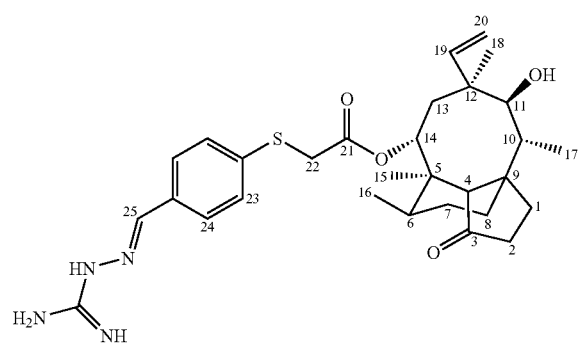

Example 21

14-O-[{4-[(1-Piperazinoiminomethyl)-hydrazonomethyl]-phenylsulfanyl}-acetyl]-mutilin hydrochloride

¹H-NMR (400 MHz, DMSO-d$_6$, δ, ppm, characteristic signals): 0.56 (d, 3H, J=7 Hz, CH$_3$-16); 0.78 (d, 3H, J=7 Hz, CH$_3$-17); 0.98 (s, 3H, CH$_3$-18); 1.29 (s, 3H, CH$_3$-15); 2.36 (bs, 1H, H-4); 3.22 (m, 4H, CH$_2$-27); 3.37 (t, 1H, J=6 Hz, H-11); 3.85 (m, 4H, CH$_2$-26), AB-system (u$_A$=3.95, u$_B$=3.89, J=24 Hz, CH$_2$-22); 4.94 (m, 2H, H-20); 5.49 (d, 1H, J=8 Hz, H-14); 6.03 (dd, 1H, J=11 and 18 Hz, H-19); 7.40 and 7.79 (2×d, 4H, J=8 Hz, H-23 and 24); 8.54 (s, 1H, H-25).

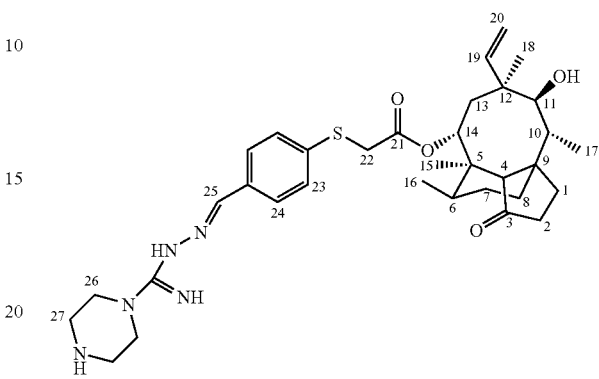

Example 22

14-O-[{4-[(1-Piperazinoiminomethyl)-methyl hydrazonomethyl]-phenylsulfanyl}-acetyl]-mutilin hydrochloride

¹H-NMR (400 MHz, DMSO-d$_6$, δ, ppm, characteristic signals): 0.55 (d, 3H, J=7 Hz, CH$_3$-16); 0.79 (d, 3H, J=7 Hz, CH$_3$-17); 0.99 (s, 3H, CH$_3$-18); 1.30 (s, 3H, CH$_3$-15); 2.36 (bs, 1H, H-4); 3.24 (m, 4H, CH$_2$-28); 3.37 (s, 3H, CH$_3$-26), 3.37 (t, 1H, J=6 Hz, H-11); 3.70 (m, 4H, CH$_2$-27); AB-system (u$_A$=3.94, u$_B$=3.88, J=21 Hz, CH$_2$-22); 4.95 (m, 2H, H-20); 5.51 (d, 1H, J=8 Hz, H-14); 6.04 (dd, 1H, J=11 and 18 Hz, H-19); 7.40 and 7.73 (2×d, 4H, J=8 Hz, H-23 and 24); 8.10 (s, 1H, H-25).

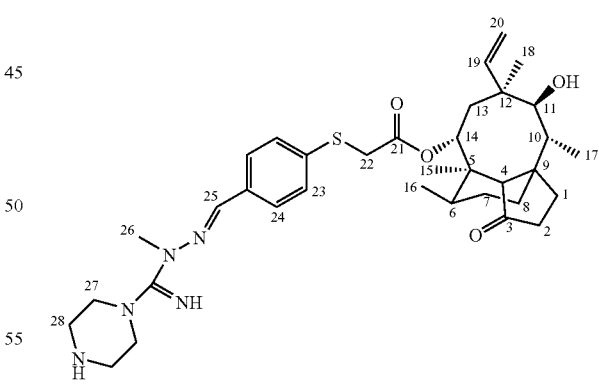

Example 23

14-O-[{3-[(1-Acetylpiperazinoiminomethyl)-hydrazonomethyl]-phenylsulfanyl}-acetyl]-mutilin hydrochloride

¹H-NMR (400 MHz, CD$_3$OD, δ, ppm, characteristic signals): 0.63 (d, 3H, J=7 Hz, CH$_3$-16); 0.87 (d, 3H, J=7 Hz, CH$_3$-17); 1.04 (s, 3H, CH$_3$-18); 1.34 (s, 3H, CH$_3$-15); 2.13 (s, 3H, CH$_3$-30), AB-system (u$_A$=3.51, u$_B$=3.33, J=67 Hz, CH$_2$-22); 3.50 (t, 1H, J=6 Hz, H-11); 3.55-3.69 (m, 8H, CH$_2$-28 and 29); 5.01 and 5.12 (2×m, 2H, H-20); 5.65 (d, 1H, J=8 Hz, H-14); 6.21 (dd, 1H, J=11 and 17 Hz, H-19); 7.28 (m, 1H, H-25); 7.33 and 7.48 (2×m, 2H, H-24 and 26); 7.74 (m, 1H, H-23); 8.18 (s, 1H, H-27).

The required 1-Acetylpiperazinoiminomethyl-hydrazine is prepared in analogy to the previously described 1-Formylpiperazinoiminomethyl-hydrazine (WO 9635692).

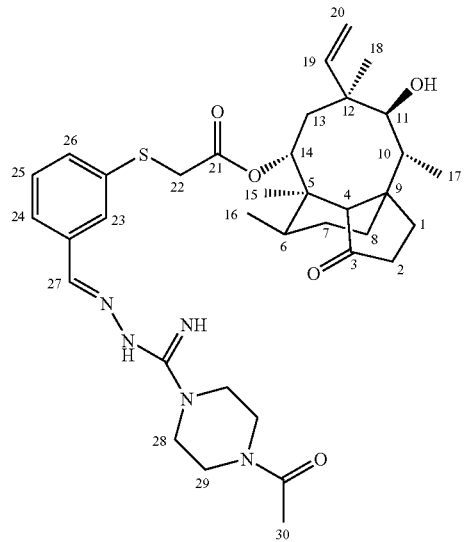

Example 24
14-O-[(3-Acetoxymethyl-phenylsulfanyl)-acetyl]-mutilin

To a solution of 1 g (2 mmol) of 14-O-[(3-Hydroxymethyl-phenylsulfanyl)-acetyl]-mutilin in 10 mL of CH$_2$Cl$_2$ are added 351 μL (3.2 mmol) of N-methylmorpholine and 302 μL (3.2 mmol) of acetic anhydride together with a catalytic amount of 4-dimethylaminopyridine. The reaction mixture was allowed to stand for 16 h at ambient temperature, concentrated under reduced pressure and chromatographed on silica using CH$_2$Cl$_2$/MeOH 100:0.5 → 100:1 as mobile phase.

$^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.98 (s, 3H, CH$_3$-18); 1.30 (s, 3H, CH$_3$-15); 2.05 (s, 3H, CH$_3$-28); 2.35 (bs, 1H, H-4); 3.37 (t, 1H, J=6 Hz, H-11); AB-system (u$_A$=3.85, u$_B$=3.78, J=29 Hz, CH$_2$-22); 4.97 (m, 2H, H-20); 5.00 (s, 2H, CH$_2$-27); 5.49 (d, 1H, J=8 Hz, H-14); 6.03 (dd, 1H, J=11 and 18 Hz, H-19); 7.13-7.28 (m, 3H, H-24, 25, and 26); 7.33 (bs, 1H, H-23).

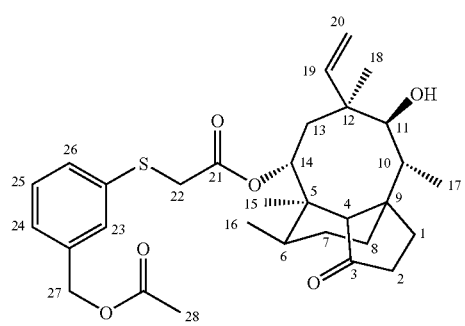

Example 25

14-O-{[3-(2-Hydroxyphenylcarbonyl)-hydroxymethyl-phenylsulfanyl]-acetyl}-mutilin To 276 mg (2 mmol) of salicylic acid suspended in 15 mL of CH$_2$Cl$_2$ 122 mg (1 mmol) of 4-dimethylaminopyridine, 500 mg (1 mmol) of 14-O-[(3-Hydroxymethyl-phenylsulfanyl)-acetyl]-mutilin and 515 mg (2.5 mmol) of dicyclohexylcarbodiimide are added. The reaction mixture is allowed to stand for 24 h at ambient temperature. After concentrating under reduced pressure, water and ethyl acetate are added and the organic phase is washed several times with water and brine. After concentration under reduced pressure the residue is chromatograped on silica using CH$_2$Cl$_2$/MeOH 100:1 as mobile phase.

$^1$H-NMR (400 MHz, DMSO-d$_6$, δ, ppm, characteristic signals)-0.53 (d, 3H, J=7 Hz, CH$_3$-16); 0.77 (d, 3H, J=7 Hz, CH$_3$-17); 0.95 (s, 3H, CH$_3$-18); 1.27 (s, 3H, CH$_3$-15); 2.30 (bs, 1H, H-4); 3.34 (t, 1H, J=6 Hz, H-11); AB-system (u$_A$=3.88, u$_B$=3.79, J=26 Hz, CH$_2$-22); 4.92 (m, 2H, H-20); 5.46 (d, 1H, J=8 Hz, H-14); 6.02 (m, 1H, H-19); 6.88-7.80 (m, 8H, arom-H).

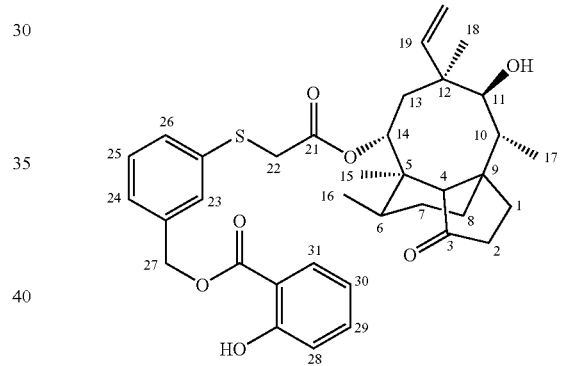

Example 26

14-O-[(3-Mercaptomethyl-phenylsulfanyl)-acetyl}-mutilin

Step 1: 14-O-[(3-Methanesulfonyloxymethyl-phenylsulfanyl)-acetyl]-mutilin

To 6 g (12 mmol) of 14-O-[(3-Hydroxymethyl-phenylsulfanyl)-acetyl]-mutilin in 250 mL of dry THF 2.17 mL (20 mmol) of N-methylmorpholine and 3.06 g (18 mmol) of methanesulfonic anhydride are added together with a catalytic amount of 4-dimethylaminopyridine. The reaction mixture is allowed to stand for 2 h at ambient temperature. After addition of Water the mixture is extracted with ethyl acetate and then the organic phase washed several times with water and brine. The organic phase is dried with anhydrous sodium sulfate and concentrated under reduced pressure. The crude product is used for the next step without further purification.

¹H-NMR (400 MHz, CDCl₃, δ, ppm, characteristic signals): 0.68 (d, 3H, J=7 Hz, CH₃-16); 0.87 (d, 3H, J=7 Hz, CH₃-17); 1.12 (s, 3H, CH₃-18); 1.40 (s, 3H, CH₃-15); 2.08 (bs, 1H, H-4); 2.96 (s, 3H, CH₃-28); 3.34 (d, 1H, J=6 Hz, H-11); 3.59 (s, 2H, CH₂-22); 5.15 and 5.30 (2×m, 2H, H-20); 5.72 (d, 1H, J=8 Hz, H-14); 6.40 (dd, 1H, J=11 and 17 Hz, H-19); 7.23-7.43 (m, 4H, arom-H).

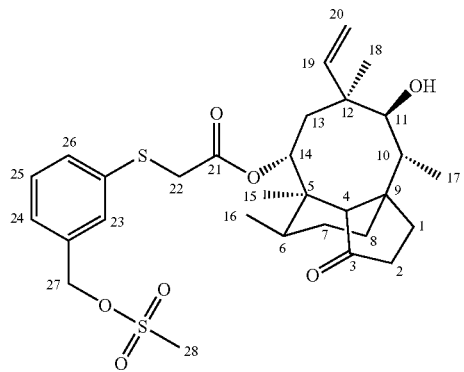

Step 2: 14-O-[(3-Tritylsulfanylmethyl-phenylsulfanyl)-acetyl]-mutilin

To 118 mg (1.73 mmol) of NaOEt in 5 mL of absolute ethanol 478 mg (1.73 mmol) of triphenylmethanethiol in 8 mL of absolute ethanol is added and the resulting solution stirred at ambient temperature. After 45 minutes 1 g (1.73 mmol) of 14-O-[(3-Methanesulfonyloxymethyl-phenylsulfanyl)-acetyl]-mutilin in 9 mL of acetone is added and the reaction is kept at ambient temperature for 3 h. After concentrating under reduced pressure, water and ethyl acetate are added and the organic phase is washed several times with water and brine. After concentration under reduced pressure the crude product is used for the next step without further purification.

¹H-NMR (400 MHz, CDCl₃, δ, ppm, characteristic signals): 0.66 (d, 3H, J=7 Hz, CH₃-16); 0.85 (d, 3H, J=7 Hz, CH₃-17); 1.07 (s, 3H, CH₃-18); 1.38 (s, 3H, CH₃-15); 2.03 (bs, 1H, H-4); 3.26 (s, 2H, CH₂-27); 3.29 (d, 1H, H-11, J=6 Hz); 3.54 (d, 2H, J=8 Hz, CH₂-22); 5.09 and 5.26 (2×m, 2H, H-20); 5.68 (d, 1H, J=8 Hz, H-14); 6.38 (dd, 1H, J=11 and 18 Hz, H-19); 6.95, and 7.20 (2×m, 2H, H-24 and 26); 7.10 (m, 1H, H-23); 7.13 (t, 1H, J=7 Hz, H-25); 7.22-7.30 (m, 15H, Trityl-H).

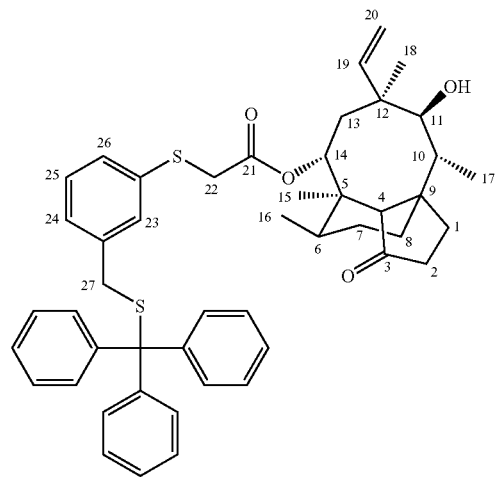

Step 3: 14-O-[(3-Mercaptomethyl-phenylsulfanyl)-acetyl]-mutilin

To 600 mg (0.79 mmol) of 14-O-[(3-Tritylsulfanylmethyl-phenylsulfanyl)-acetyl]-mutilin dissolved in 15 mL of a 1:1 mixture of TFA/CH₂Cl₂ 630 μL (3.95 mmol) of triethylsilane is added. The reaction mixture is allowed to stand at ambient temperature for 2 h. After concentrating at reduced pressure, the residue is chromatographed on silica using cyclohexane/ethyl acetate 7:3 as mobile phase.

¹H-NMR (400 MHz, DMSO-d₆, δ, ppm, characteristic signals): 0.57 (d, 3H, J=7 Hz, CH₃-16); 0.79 (d, 3H, J=7 Hz, CH₃-17); 0.98 (s, 3H, CH₃-18); 1.30 (s, 3H, CH₃-15); 2.37 (bs, 1H, H-4); 3.38 (t, 1H, J=6 Hz, H-11); 3.66 (d, 2H, J=8 Hz, CH₂-27); AB-system (u$_A$=3.84, u$_B$=3.77, J=27 Hz, CH₂-22); 4.95 (m, 2H, H-20); 5.49 (d, 1H, J=8 Hz, H-14); 6.03 (dd, 1H, J=11 and 18 Hz, H-19); 7.12-7.26 (m, 3H, H-24, 25 and 26); 7.31 (bs, 1H, H-23).

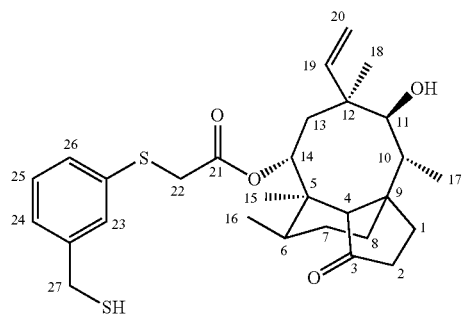

Example 27

14-O-[(3-Acetylthiomethyl-phenylsulfanyl)-acetyl]-mutilin

To 579 mg (1 mmol) of 14-O-[(3-Methanesulfonyloxymethyl-phenylsulfanyl)-acetyl]-mutilin in 100 mL of THF 114 mg of potassium thioacetate is added. After stirring for 24 h at ambient temperature, the reaction mixture is concentrated under reduced pressure. Ethyl acetate and water are added and the organic phase is washed several times with water and brine. After concentrating under reduced pressure, the residue is chromatographed on silica using CH₂Cl₂/MeOH 100:1 as mobile phase.

¹H-NMR (400 MHz, DMSO-d₆, δ, ppm, characteristic signals): 0.55 (d, 3H, J=7 Hz, CH₃-16); 0.79 (d, 3H, J=7 Hz, CH₃-17); 0.98 (s, 3H, CH₃-18); 1.29 (s, 3H, CH₃-15); 2.33 (s, 3H, CH₃-28); 2.35 (bs, 1H, H-4); 3.37 (t, 1H, J=6 Hz, H-11); AB-system (u$_A$=3.82, u$_B$=3.76, J=26 Hz, CH₂-22); 4.04 (s, 2H, CH₂-27); 4.94 (m, 2H, H-20); 5.49 (d, 1H, J=8 Hz, H-14); 6.03 (dd, 1H, J=11 and 18 Hz, H-19); 7.08 (m, 1H, H-25); 7.22 (m, 2H, H-24 and 26); 7.26 (bs, 1H, H-23).

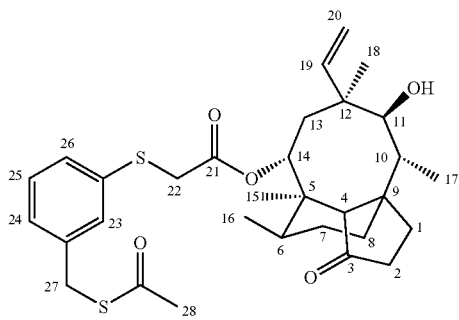

Example 28

14-O-[(3-Azidomethyl-phenylsulfanyl)-acetyl]-mutilin

To 1 g (1.73 mmol) of 14-O-[(3-Methanesulfonyloxymethyl-phenylsulfanyl)-acetyl]-mutilin in 10 mL of DMF 449 mg of $NaN_3$ is added. The resulting suspension is stirred for 4.5 h at 50° C. and left overnight at ambient temperature. Water and ethyl acetate are added and the organic phase washed several times with water and brine. After concentrating under reduced pressure, the residue is chromatographed on silica using $CH_2Cl_2$/MeOH 100:1 as mobile phase.

$^1$H-NMR (400 MHz, DMSO-$d_6$, δ, ppm, characteristic signals): 0.56 (d, 3H, J=7 Hz, $CH_3$-16); 0.79 (d, 3H, J=7 Hz, $CH_3$-17); 1.00 (s, 3H, $CH_3$-18); 1.30 (s, 3H, $CH_3$-15); 2.34 (bs, 1H, H-4); 3.37 (t, 1H, J=6 Hz, H-11); AB-system ($u_A$=3.85, $u_B$=3.78, J=27 Hz, $CH_2$-22); 4.39 (s, 2H, $CH_2$-27); 4.95 (m, 2H, H-20); 5.49 (d, 1H, J=8 Hz, H-14); 6.04 (dd, 1H, J=11 and 18 Hz, H-19); 7.18 (m, 1H, H-25); 7.32 (m, 2H, H-24 and 26); 7.34 (bs, 1H, H-23).

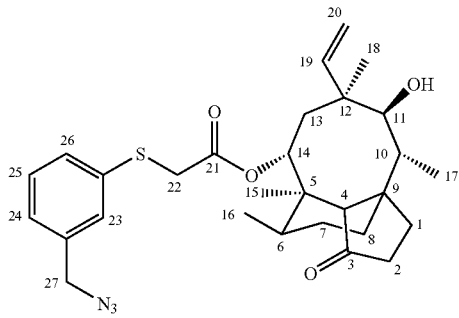

Example 29

14-O-[(3-Aminomethyl-phenylsulfanyl)-acetyl]-mutilin hydrochloride 1 g (1.9 mmol) of 14-O-[(3-Azidomethyl)-phenylsulfanyl-acetyl]-mutilin is dissolved in 30 mL of THF, 900 mg of Lindlar-catalyst is added and the reaction mixture hydrogenated for 6 h. The reaction mixture is filtered through celite, concentrated under reduced pressure and the residue is chromatographed on silica using $CH_2Cl_2$/MeOH 10:1 as mobile phase. The hydrochloride was obtained by dissolving 125 mg of 14-O-[(3-Aminomethyl)-phenylsulfanyl-acetyl]-mutilin in 3 mL of $CH_2Cl_2$ and adding 2 mL of HCl-saturated $Et_2O$. After 45 minutes the reaction was evaporated to dryness under reduced pressure.

$^1$H-NMR (400 MHz, DMSO-$d_6$, δ, ppm, characteristic signals): 0.57 (d, 3H, J=7 Hz, $CH_3$-16); 0.79 (d, 3H, J=7 Hz, $CH_3$-17); 1.00 (s, 3H, $CH_3$-18); 1.31 (s, 3H, $CH_3$-15); 2.38 (bs, 1H, H-4); 3.38 (t, 1H, J=6 Hz, H-11); AB-system ($u_A$=3.89, $u_B$=3.82, J=26 Hz, $CH_2$-22); 3.95 (s, 2H, $CH_2$-27); 4.98 (m, 2H, H-20); 5.51 (d, 1H, J=8 Hz, H-14); 6.05 (dd, 1H, J=11 and 18 Hz, H-19); 7.30 (m, 3H, H-24, 25 and 26); 7.48 (s, 1H, H-23).

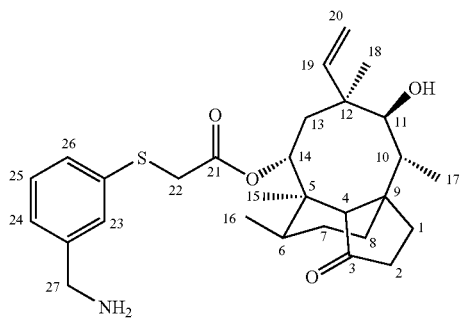

Example 30

14-O-[(3-Acetylaminomethyl-phenylsulfanyl)-acetyl]-mutilin

To 300 mg (0.6 mmol) of 14-O-[(3-Aminomethyl)-phenylsulfanyl-acetyl]-mutilin in 3 mL of $CH_2Cl_2$ 106 μL (0.96 mmol) of N-methylmorpholine, 91 μL (0.96 mmol) of acetic anhydride and a catalytic amount of 4-dimethylaminopyridine are added. The resulting solution is allowed to stand for 5 h at ambient temperature. After evaporation to dryness under reduced pressure, the residue is chromatographed on silica using $CH_2Cl_2$/MeOH 100:1 ⟶ 100:1.2 as mobile phase.

$^1$H-NMR (400 MHz, DMSO-$d_6$, δ, ppm, characteristic signals): 0.56 (d, 3H, J=7 Hz, $CH_3$-16); 0.79 (d, 3H, J=7 Hz, $CH_3$-17); 0.99 (s, 3H, $CH_3$-18); 1.30 (s, 3H, $CH_3$-15); 1.85 (s, 3H, $CH_3$-28); 2.35 (bs, 1H, H-4); 3.38 (t, 1H, J=6 Hz, H-11); AB-system ($u_A$=3.82, $u_B$=3.75, J=28 Hz, $CH_2$-22); 4.18 (d, 2H, J=6 Hz, $CH_2$-27); 4.95 (m, 2H, H-20); 5.49 (d, 1H, J=8 Hz, H-14); 6.04 (dd, 1H, J=11 and 19 Hz, H-19); 7.03-7.26 (m, 4H, H-23, 24, 25 and 26).

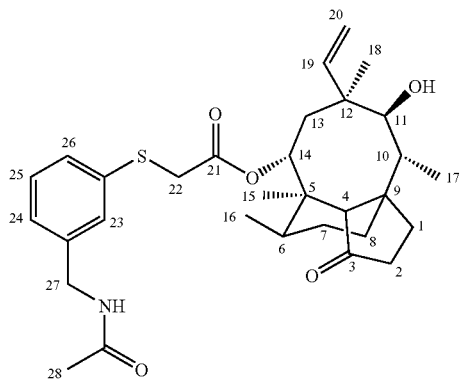

Using acetic formic anhydride, the following example is prepared in a similar fashion:

Example 31

14-O-[(3-Formylaminomethyl-phenylsulfanyl)-acetyl]-mutilin $^1$H-NMR (400 MHz, DMSO-$d_6$, δ, ppm, characteristic signals): 0.57 (d, 3H, J=7 Hz, CH$_3$-16); 0.80 (d, 3H, J=7 Hz, CH$_3$-17); 1.00 (s, 3H, CH$_3$-18); 1.30 (s, 3H, CH$_3$-15); 2.35 (bs, 1H, H-4); 3.37 (t, 1H. J=6 Hz, H-11); AB-system (u$_A$=3.85, u$_B$=3.77, J=26 Hz, CH$_2$-22); 4.24 (d, 2H, J=6 Hz, CH$_2$-27); 4.95 (m, 2H, H-20); 5.49 (d, 1H, J=8 Hz, H-14); 6.05 (dd, 1H, J=11 and 19 Hz, H-19); 7.03-7.38 (m, 4H, H-23, 24, 25 and 26), 8.11 (s, 1H, H-28).

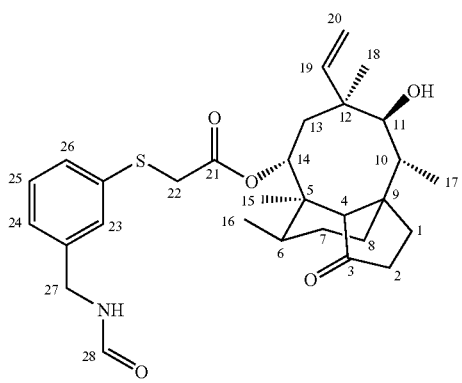

Example 32

14-O-[{3-[(2-Hydroxy-ethylamino)-methyl]-phenyl-sulfanyl}-acetyl]-mutilin hydrochloride To 579 mg (1 mmol) of 14-O-[(3-Methanesulfonyloxymethyl-phenylsulfanyl)-acetyl]-mutilin in 20 mL of THF 112 mg (2 mmol) of 2-Amino-ethanol are added and the reaction is stirred at ambient temperature for 16 h. After concentration under reduced pressure ethyl acetate and water are added and the organic phase is washed several times with water and brine. The organic phase is dried with anhydrous sodium sulfate, evaporated under reduced pressure and the residue chromatographed on silica using CH$_2$Cl$_2$/MeOH/aqu. NH$_3$ 100:5:0.05 as mobile phase. The hydrochloride was obtained as exemplified for example 29.

$^1$H-NMR (400 MHz, DMSO-$d_6$, δ, ppm, characteristic signals): 0.57 (d, 3H, J=7 Hz, CH$_3$-16); 0.79 (d, 3H, J=7 Hz, CH$_3$-17); 0.98 (s, 3H, CH$_3$-18); 1.30 (s, 3H, CH$_3$-15); 2.35 (bs, 1H, H-4); 2.53 (t, 2H, J=6 Hz, CH$_2$-28); 3.38 (m, 5H, H-11, CH$_2$-28 and 29); 3.44 (q, 2H, J=6 and 10 Hz, CH$_2$-29); 3.65 (S, 3H, CH$_2$-27); AB-system (u$_A$=3.82, u$_B$=3.74, J=27 Hz, CH$_2$-22); 4.95 (m, 2H, H-20); 5.49 (d, 1H, J=8 Hz, H-14); 6.04 (dd, 1H, J 11 and 18 Hz, H-19); 7.18 (m, 3H, H-24, 25 and 26); 7.29 (s, 1H. H-23).

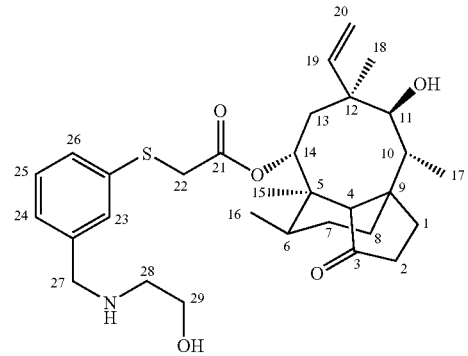

The following compounds are prepared in a similar fashion:

Example 33

14-O-[{3-[(3-Amino-propylamino)-methyl]-phenyl-sulfanyl}-acetyl]-mutilin hydrochloride $^1$H-NMR (400 MHz, DMSO-$d_6$, δ, ppm, characteristic signals): 0.56 (d, 3H, J=7 Hz, CH$_3$-16); 0.79 (d, 3H, J=7 Hz, CH$_3$-17); 0.98 (s, 3H, CH$_3$-18); 1.30 (s, 3H, CH$_3$-15); 2.35 (bs, 1H, H-4); 2.48 and 2.57 (2×m, 4H, CH$_2$-28 and 30); 3.36 (t, 1H, J=6 Hz, H-11); 3.60 (s, 2H, CH$_2$-27); AB-system (u$_A$=3.81, u$_B$=3.743, J=28 Hz, CH$_2$-22); 4.95 (m, 2H, H-20); 5.49 (d, 1H, J=8 Hz, H-14); 6.03 (dd, 1H, J=11 and 17 Hz, H-19); 7.10-7.23 (m, 3H, H-24, 25 and 26); 7.28 (s, 1H, H-23).

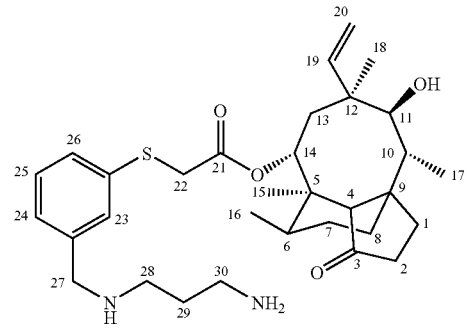

Example 34

14-O-[(3-{[3-(3-Amino-propylamino)-propylamino-methyl}-phenylsulfanyl)-acetyl]-mutilin hydrochloride $^1$H-NMR (400 MHz, DMSO-$d_6$, δ, ppm, characteristic signals): 0.57 (d, 3H, J=7 Hz, CH$_3$-16); 0.79 (d, 3H, J=7 Hz, CH$_3$-17); 1.00 (s, 3H, CH$_3$-18), 1.31 (S, 3H, CH$_3$-15); 2.38 (s, 1H, H-4); 2.86-3.05 (m, OH, CH$_2$-28, 30, 31 and 33); 3.76 (bt, 1H, J=6 Hz, H-11); AB-system (u$_A$=3.92, u$_B$=3.84, J=27 Hz, CH$_2$-22); 4.06 (bs, 2H, CH$_2$-27); 4.97 (m, 2H, H-20); 5.51 (d, 1H, J=8 Hz, H-14); 6.04 (dd, 1H, J=11 and 18 Hz, H-19); 7.36 (m, 3H, H-24, 25 and 26); 7.60 (s, 1H, H-23).

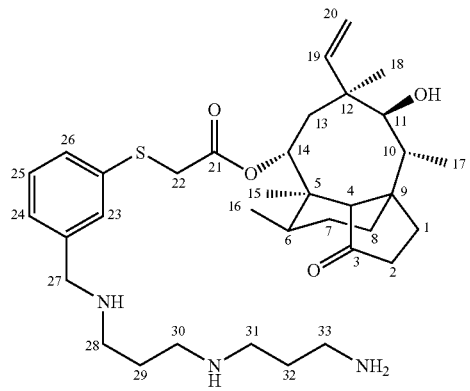

Example 35

14-O-[{3-[2,2-Difluoro-ethylamino)-methyl]-phenylsulfanyl}-acetyl]-mutilin hydrochloride $^1$H-NMR (400 MHz, DMSO-d$_6$, δ, ppm, characteristic signals): 0.55 (d, 3H, J=7 Hz, CH$_3$-16); 0.79 (d, 3H, J=7 Hz, CH$_3$-17); 0.97 (s, 3H, CH$_3$-18); 1.29 (s, 3H, CH$_3$-15); 2.34 (bs, 1H, H-4); 2.79 (bt, 2H, J=16 Hz, CH$_2$-28); 3.48 (t, 1H, J=6 Hz, H-11); 3.68 (s, 2H, CH$_2$-27); AB-system (u$_A$=3.83, u$_B$=3.77, J=30 Hz, CH$_2$-22); 4.94 (m, 2H, H-20); 5.49 (d, 1H, J=8 Hz, H-14); 5.97 (tt, 1H, J=4 and 56 Hz, H-29); 6.03 (dd, 1H, J=11 and 11 Hz, H-19); 7.10-7.28 (m, 3H, H-24, 25 and 26); 7.30 (s, 1H, H-23)

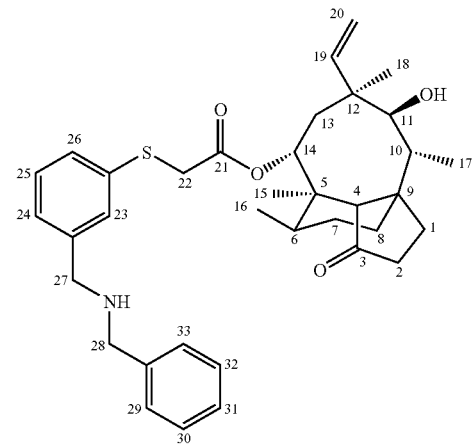

Example 37

14-O-[(3-Allylaminomethyl-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 1.00 (s, 3H, CH$_3$-18); 1.30 (s, 3H, CH$_3$-15); 2.35 (bs, 1H, H-4); 3.37 (t, 1H, J=6 Hz, H-11); 3.54 (d, 2H, J=7 Hz, CH$_2$-28); AB-system (u$_A$=3.90, u$_B$=3.83, J=26 Hz, CH$_2$-22); 4.04 (s, 2H, CH$_2$-27); 4.97 (m, 2H, H-20); 5.43 (m, 2H, H-30); 5.50 (d, 1H, J=8 Hz, H-14); 5.90 (m, 1H, H-29); 6.04 (dd, 1H, J=11 and 18 Hz, H-19); 7.35 (m, 3H, H-24, 25 and 26); 7.53 (d, 1H, J=1 Hz, H-23).

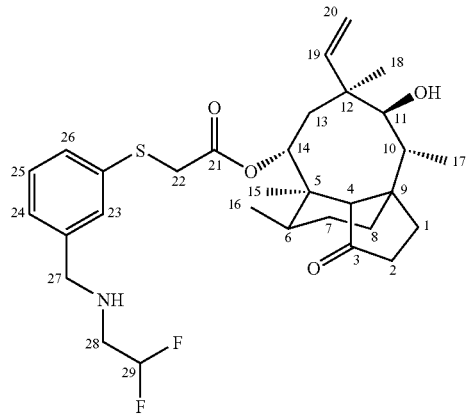

Example 36

14-O-[(3-Benzylaminomethyl-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 1.00 (s, 3H, CH$_3$-18); 1.30 (s, 3H, CH$_3$-15); 2.35 (bs, 1H, H-4); 3.37 (t, 1H, J=6 Hz, H-11); AB-system (u$_A$=3.89, u$_B$=3.83, J=26 Hz, CH$_2$-22); 4.09 (m, 4H, CH$_2$-27 and 28); 4.95 (m, 2H, H-20); 5.50 (d, 1H, J=8 Hz, H-14); 6.04 (dd, 1H, J=8 and 20 Hz, H-19); 7.32-7.56 (m, 9H, arom-H).

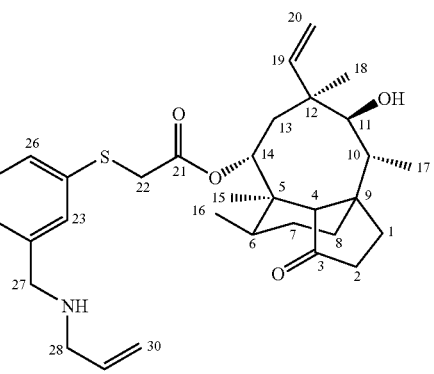

Example 38

14-O-{[3-(2-Methoxy-ethylamino)-methyl-phenylsulfanyl]-acetyl}-mutilin hydrochloride $^1$H-NMR (400 MHz, DMSO-d$_6$, δ, ppm, characteristic signals): 0.57 (d, 3H, J=7 Hz, CH$_3$-16); 0.80 (d, 3H, J=7 Hz, CH$_3$-17); 0.99 (s, 3H, CH$_3$-18); 1.30 (s, 3H, CH$_3$-15); 2.36 (bs, 1H, H-4), 3.01 (t, 2H, J=5 Hz, CH$_2$-28); 3.28 (s, 3H, CH$_3$-30); 3.38 (t, 1H, J=6 Hz, H-11); 3.59 (t, 2H, J A 5 Hz, H-29); AB-system (u$_A$=3.89, u$_B$=3.83, J=26 Hz, CH$_2$-22); 4.07 (s, 2H, CH$_2$-27); 4.97 (m, 2H, H-20); 5.50 (d, 1H, J=8 Hz, H-14); 6.04 (dd, 1H, J=10 and 21 Hz, H-19); 7.34 (m, 3H, H-24, 25 and 26); 7.56 (bs, 1H, H-23).

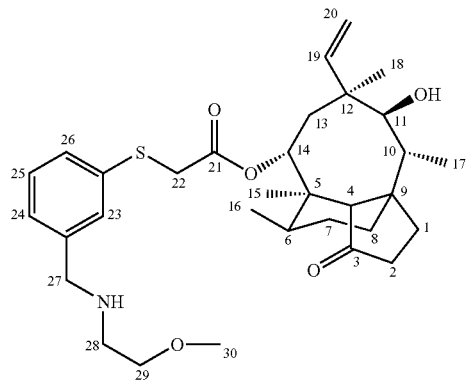

Example 39

14-O-[(3-{[2-(2-Amino-ethylamino)-ethylamino]-methyl}-phenylsulfanyl)-acetyl]-mutilin hydrochloride $^1$H-NMR (500 MHz, DMSO-d$_6$, δ, ppm, characteristic signals): 0.57 (d, 3H, J=7 Hz, CH$_3$-16); 0.79 (d, 3H, J=7 Hz, CH$_3$-17); 1.00 (s, 3H, CH$_3$-18); 1.31 (s, 3H, CH$_3$-15); 2.37 (bs, 1H, H-4); 3.13-3.36 (m, 8H, CH$_2$-28, 29, 30 and 31); 3.37 (t, 1H, J=6 Hz, H-11); AB-system (u$_A$=3.92, u$_B$=3.84, J=32 Hz, CH$_2$-22); 4.15 (s, 2H, CH$_2$-27); 4.96 (m, 2H, H-20); 5.52 (d, 1H, J=8 Hz, H-14); 6.06 (dd, 1H, J=11 and 18 Hz, H-19); 7.37 (m, 3H, H-24, 25 and 26); 7.59 (s, 1H, H-23).

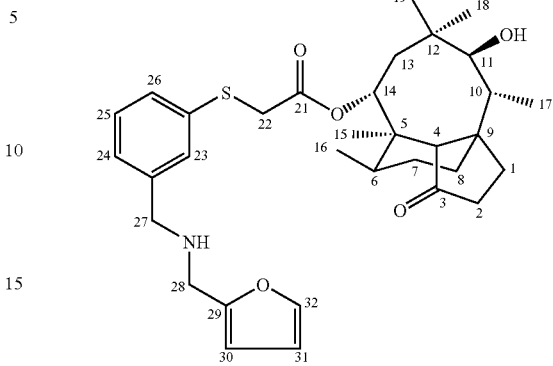

Example 41

14-O-[(3-Methylaminomethyl-phenylsulfanyl)-acetyl]-mutilin hydrochloride $^1$H-NMR (400 MHz, DMSO-d$_6$, δ, ppm, characteristic signals): 0.57 (d, 3H, J=7 Hz, CH$_3$-16); 0.81 (d, 3H, J=7 Hz, CH$_3$-17); 0.99 (s, 3H, CH$_3$-18); 1.31 (s, 3H, CH$_3$-15); 2.36 (bs, 1H, H-4); 2.50 (s, 3H, CH$_3$-28); 3.38 (t, 1H, J=6 Hz, H-11); AB-system (u$_A$=3.90, u$_B$=3.83, J=26 Hz, CH$_2$-22); 4.07 (s, 2H, CH$_2$-27); 4.95 (m, 2H, H-20); 5.50 (d, 1H, J=8 Hz, H-14); 6.05 (dd, 1H, J=11 and 18 Hz, H-19); 7.33 (m, 3H, H-24, 25 and 26); 7.53 (s, 1H, H-23).

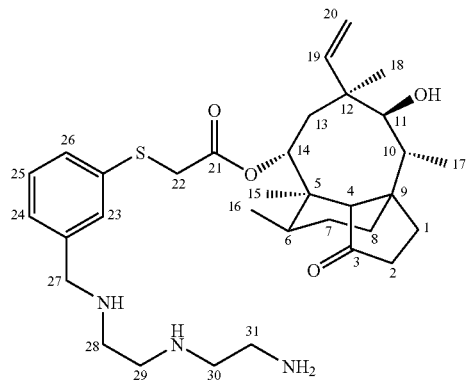

Example 40

14-O-[3-{[(Furan-2-ylmethyl)-amino]-methyl}-phenylsulfanyl-acetyl]-mutilin hydrochloride $^1$H-NMR (400 MHz, DMSO-d$_6$, δ, ppm, characteristic signals): 0.57 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.37 (t, 1H, J=6 Hz, H-11); AB-system (u$_A$=3.90, u$_B$=3.83, J=26 Hz, CH$_2$-22); 4.07 and 4.18 (2×s, 4H, CH$_2$-27 and 28); 4.95 (m, 2H, H-20); 5.50 (d, 1H, J=8 Hz, H-14); 6.05 (dd, 1H, J=11 and 18 Hz, H-19); 6.53 and 6.63 (2×m, 2H, H-30 and 31); 7.34 (m, 3H, H-24, 25 and 26); 7.52 (s, 1H, H-23); 7.76 (m, 1H, H-32).

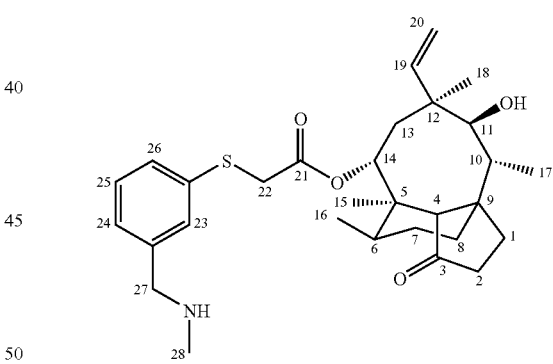

Example 42

14-O-[(3-Cyclopropylaminomethyl-phenylsulfanyl)-acetyl]-mutilin hydrochloride $^1$H-NMR (400 MHz, DMSO-d$_6$, δ, ppm, characteristic signals): 0.57 (d, 3H, J=7 Hz, CH$_3$-16); 0.70, 0.85 (2×m, 4H, CH$_2$-29,30); 0.79 (d, 3H, J=7 Hz, CH$_3$-17); 1.00 (s, 3H, CH$_3$-18); 1.31 (s, 3H, CH$_3$-15); 2.37 (bs, 1H, H-4); 2.60 (m, 1H, H-28); 3.37 (t, 1H, J=6 Hz, H-11); AB-system (u$_A$=3.90, u$_B$=3.83, J=27 Hz, CH$_2$-22); 4.14 (s, 2H, CH$_2$-27); 4.95 (m, 2H, H-20); (d, 1H, J=8 Hz, H-14); 6.05 (dd, 1H. J=11 and 18 Hz, H-19); 7.34 (s, 3H, H-24, 25 and 26); 7.53 (s, 1H, H-28).

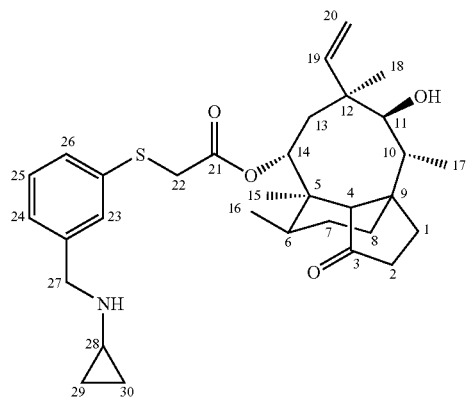

Example 43

14-O-[(3-Morpholin-4-yl-methyl-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.29 (s, 3H, CH$_3$-15); 2.35 (bs, 1H, H-4); 2.98-3.23 (m, 4H, CH$_2$-28 and 31); 3.35 (t, 1H, J=6 Hz, H-11); 3.70-3.96 (m, 6H, CH$_2$-22,29 and 30); 4.27 (m, 2H, CH$_2$-27); 4.95 (m, 2H, H-20); 5.50 (d, 1H, J=8 Hz, H-14); 6.03 (dd, 1H, J=11 and 19 Hz, H-19); 7.40 (m, 3H, H-24, 25 and 26), 7.63 (s, 1H, H-28).

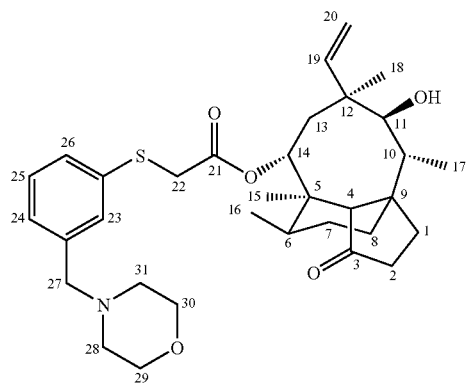

Example 44

14-O-[(3-piperazin-1-ylmethyl-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 1.00 (s, 3H, CH$_3$-18); 1.28 (s, 3H, CH$_3$-15); 2.23 and 2.66 (m, t, 8H, J=5 Hz, CH$_2$-28,29,30 and 31); 2.34 (bs, 1H, H-4); 3.35 (m, 3H, H-11, CH$_2$-27); AB-system (u$_A$=3.80, u$_B$=3.73, J=24 Hz, CH$_2$-22); 4.27 (m, 2H, CH$_2$-27); 4.95 (m, 2H, H-20); 5.49 (d, 1H, J=8 Hz, H-14); 6.02 (dd, 1H, J=11 and 18 Hz, H-19); 7.08-7.27 (m, 4H, H-23,24,25 and 26).

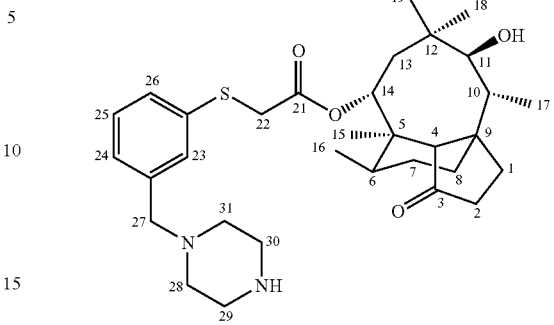

Example 45

14-O-{3-[(2-Dimethylamino-ethylamino)-methyl]-phenylsulfanyl-acetyl}-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 1.00 (s, 3H, CH$_3$-18); 1.31 (s, 3H, CH$_3$-15); 2.37 (bs, 1H, H-4); 2.82 (s, 6H, CH$_3$-30 and 31); 3.38 (m, 5H, H-11, CH$_2$-28 and 29); AB-system (u$_A$=3.92, u$_B$=3.83, J=27 Hz, CH$_2$-22); 4.13 (m, 2H, CH$_2$-27); 4.97 (m, 2H, H-20); 5.51 (d, 1H, J=8 Hz, H-14); 6.05 (dd, 1H, J=11 and 18 Hz, H-19); 7.38 (m, 3H, H-24, 25 and 26); 7.59 (s, 1H, H-23).

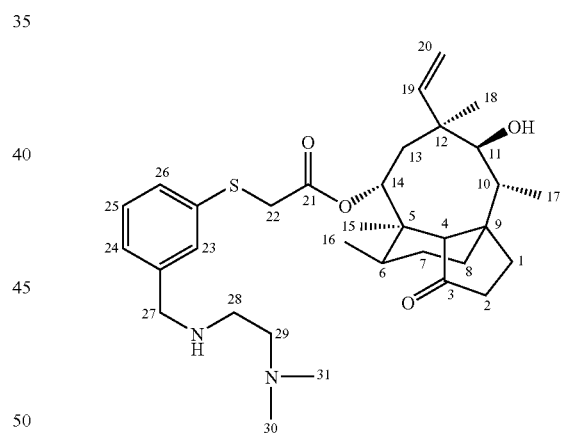

Example 46

14-O-{3-[(2-Amino-ethylamino)-methyl]-phenylsulfanyl}-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.80 (d, 3H, J=7 Hz, CH$_3$-17); 0.97 (s, 3H, CH$_3$-18); 1.30 (s, 3H, CH$_3$-15); 2.35 (bs, 1H, H-4); 2.45 and 2.58 (2×m, 4H, CH$_2$-28 and 29); 3.34 (d, 1H, J=6 Hz, H-11); 3.62 (s, 2H, CH$_2$-27); AB-system (u$_A$=3.82, u$_B$=3.73, J=27 Hz, CH$_2$-22); 4.95 (m, 2H, H-20); 5.49 (d, 1H, J=8 Hz, H-14); 6.03 (dd, 1H, J=11 and 18 Hz, H-19); 7.18 (m, 3H, H-24, 25 and 26); 7.29 (s, 1H, H-23).

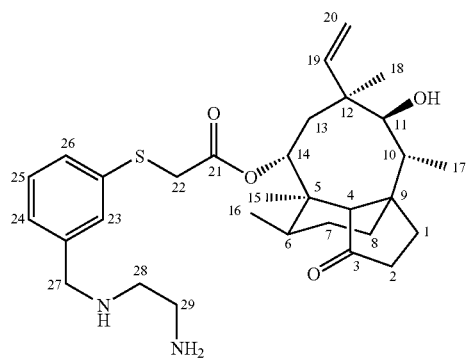

Example 47

14-O-[(3-{[Bis-(2-hydroxy-ethyl)-amino]-methyl}-phenylsulfanyl)-acetyl]-mutilin hydrochloride

$^1$H-NMR (400 MHz, DMSO-$d_6$, δ, ppm, characteristic signals): 0.56 (d, 3H, J=7 Hz, $CH_3$-16), 0.79 (d, 3H, J=7 Hz, $CH_3$-17); 0.99 (s, 3H, $CH_3$-18); 1.30 (s, 3H, $CH_3$-15); 2.36 (bs, 1H, H-4), 2.53 (t, 2H, J=6 Hz, $CH_2$-28); 3.13 and 3.23 (2×m, 4H, $CH_2$-28 and 30); 3.38 (bt, 1H, H-11, J=6 Hz); 3.78 (m, 4H, $CH_2$-29 and 31); AB-system ($u_A$=3.92, $u_B$=3.84, J=31 Hz, $CH_2$-22); 4.48 (bd, 2H, J=4 Hz, $CH_2$-27); 4.95 (m, 2H, H-20); 5.50 (d, 1H, J=8 Hz, H-14); 6.04 (dd, 1H, J=11 and 18 Hz, H-19); 7.38 (m, 4H, arom-H).

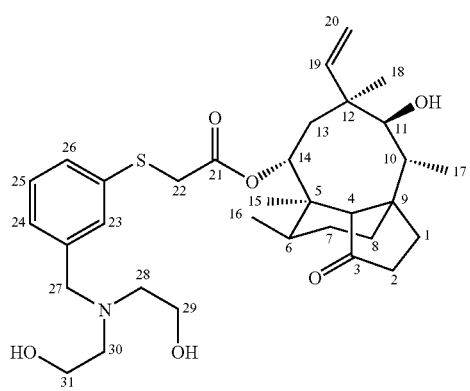

Example 48

14-O-[(3-Dimethylaminomethyl-phenylsulfanyl)-acetyl]-mutilin hydrochloride

$^1$H-NMR (400 MHz, DMSO-$d_6$, δ, ppm, characteristic signals): 0.55 (d, 3H, J=7 Hz, $CH_3$-16); 0.79 (d, 3H, J=7 Hz, $CH_3$-17); 0.97 (s, 3H, $CH_3$-18); 1.29 (s, 3H, $CH_3$-15); 2.11 (s, 6H, $CH_3$-28 and 29); 2.36 (bs, 1H, H-4); 3.31 (s, 2H, $CH_2$-27); 3.37 (t, 1H, H-11, J=6 Hz); AB-system ($u_A$=3.80, $u_B$=3.74, J=25 Hz, $CH_2$-22); 4.95 (m, 2H, H-20); 5.49 (d, 1H, J=8 Hz, H-14); 6.03 (m, 1H, H-19); 7.08 and 7.22 (2×m, 4H, arom-H).

Antimicrobial Activity of Novel Pleuromutilin-Derivatives:

The antibacterial activity expressed as minimal inhibitory concentration (MIC) was determined according to the approved standard reference recommendations of CLSI (former NCCLS).

Compound of Example 1 and the other claimed compounds exhibited very good activity against at least one of the clinical relevant bacterial pathogens *Staphylococcus aureus, Enterococcus faecalis, Streptococcus pneumoniae, Moraxelia catarrhalis* and *Escherichia coli* (see Table 1). This in vitro activity was significantly better than that of the comparator compound 2, as the MICs of Example 1 were by at least a factor of 2 lower against at least one of the strains shown in Table 1 than the MICs of Example 2 (see Table 1).

TABLE 1

Antimicrobial activity of Example 1 and the comparator compound Example 2 against selected bacterial pathogens shown as minimal inhibitory concentration (MIC, [μg/ml]).

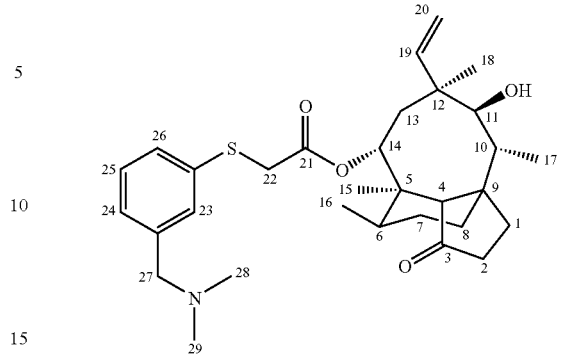

| Species | ATCC number | Strain | MIC [μg/ml] Example 1 | MIC [μg/ml] Example 2 |
|---|---|---|---|---|
| *Staphylococcus aureus* (MSSA) | ATCC10390 | B6 | ≦0.0125 | 0.025 |
| *Staphylococcus aureus* (MSSA) | ATCC29213 | B7 | ≦0.0125 | 0.025 |
| *Enterococcus faecalis* | ATCC29212 | B4 | 6.4 | >25.6 |
| *Enterococcus faecalis* | ATCC51299 | B5 | 6.4 | >25.6 |
| *Moraxella catarrhalis* | ATCC43618 | B407 | ≦0.0125 | ≦0.0125 |
| *Escherichia coli* | ATCC25922 | B1 | 12.8 | >25.6 |
| *Streptococcus pneumoniae* | ATCC49619 | B11 | 0.01 | 0.16 |

The invention claimed is:

1. A compound selected from the group consisting of
   14-O—[(((C$_{1-6}$)Alkoxy-(C$_{1-6}$)alkyl)-phenylsulfanyl)-acetyl]-mutilins,
   14-O—[(((C$_{1-6}$)Mono- or dialkylamino-(C$_{1-6}$)alkyl)-phenylsulfanyl)-acetyl]-mutilins,
   14-O—[(((C$_{1-6}$)Acylamino-(C$_{1-6}$)alkyl)-phenylsulfanyl)-acetyl]-mutilins, 14-O-[((Hydroxy-($C_{1-6}$)-alkyl)-phenylsulfanyl)-acetyl]-mutilins,
14-O-[(Formyl-($C_{0-5}$)-alkyl)-phenylsulfanyl)-acetyl]-mutilins,
14-O-[((Guanidino-imino-($C_{1-6}$)alkyl)-phenylsulfanyl)-acetyl]-mutilins,
14-O-[((Ureido-imino-($C_{1-6}$)alkyl)-phenylsulfanyl)-acetyl]-mutilins,
14-O-[((Thioureido-imino-($C_{1-6}$)alkyl)-phenylsulfanyl)-acetyl]-mutilins,
14-O-[((Isothioureido-imino-($C_{1-6}$)alkyl)-phenylsulfanyl)-acetyl]-mutilins,
14-O-[(Cyano-($C_{0-5}$)-alkyl)-phenylsulfanyl)-acetyl]-mutilins,
14-O-[(Azido-($C_{0-5}$)-alkyl)-phenylsulfanyl)-acetyl]-mutilins,
14-O—[((($C_{1-6}$)Acyloxy-($C_{1-6}$)alkyl)-phenylsulfanyl)-acetyl]-mutilins, and
14-O-[((Benzoyloxy-($C_{1-6}$)alkyl)-phenylsulfanyl)-acetyl]-mutilins,
wherein the phenyl-ring is optionally further substituted by up to four groups independently selected from halogen, ($C_{1-6}$)alkyl, aryl, aryl($C_{1-6}$)-alkyl, ($C_{1-6}$)alkoxy, ($C_{1-6}$) alkoxy($C_{1-6}$)alkyl, halo($C_{1-6}$)alkyl, aryl($C_{1-6}$)alkoxy, hydroxy, nitro, cyano, azido, acyloxy, carbamoyl, mono- or di-N—($C_{1-6}$)alkylcarbamoyl, ($C_{1-6}$)-alkoxycarbonyl, aryloxycarbonyl, ureido, guanidino, ($C_{1-6}$)alkylguanidino, amidino, ($C_{1-6}$) alkylamidino, sulphonylamino, aminosulphonyl, ($C_{1-6}$)alkylthio, ($C_{1-6}$)-alkylsulphinyl, ($C_{1-6}$) alkylsulphonyl, heterocyclyl, heteroaryl, heterocyclyl($C_{1-6}$)alkyl and heteroaryl($C_{1-6}$)alkyl, or two adjacent ring carbon atoms may be linked by a ($C_{3-5}$) alkylene chain, to form a carbocyclic ring.

2. A compound according to claim 1 which is selected from the group consisting of
14-O—[((($C_{1-6}$)Alkoxy-($C_{1-6}$)alkyl)-phenylsulfanyl)-acetyl]-mutilins,
14-O—[((($C_{1-6}$)Mono- or dialkylamino-($C_{1-6}$)alkyl)-phenylsulfanyl)-acetyl]-mutilins,
14-O-[((Hydroxy-($C_{1-6}$)-alkyl)-phenylsulfanyl)-acetyl]-mutilins,
14-O-[((Formyl-($C_{0-5}$)-alkyl)-phenylsulfanyl)-acetyl]-mutilins, and
14-O-[((Guanidino-imino-($C_{1-6}$)alkyl)-phenylsulfanyl)-acetyl]-mutilins.

3. A compound of formula (I)

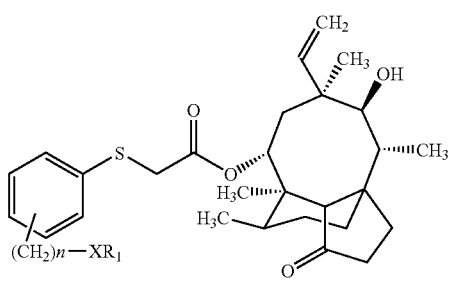

wherein
n is 1 to 6;
X is oxygen or $NR_2$ wherein $R_2$ is hydrogen or linear or branched ($C_{1-6}$)-alkyl, or hydroxy-($C_{1-6}$)alkyl or ($C_{1-6}$) alkoxy-($C_{1-6}$)alkyl,
$R_1$ is hydrogen, linear or branched ($C_{1-6}$)-alkyl, mono- or dihalogenated ($C_{1-6}$)-alkyl, amino($C_{1-6}$)-alkyl, hydroxy ($C_{1-6}$)-alkyl, phenyl($C_{1-6}$)-alkyl, ($C_{1-6}$)-alkylen, furanyl ($C_{1-6}$)-alkyl, ($C_{3-4}$)-cycloalkyl, and the corresponding ammonium salts, e.g. chlorides, or
$R_1$ and $R_2$ together with the nitrogen atom to which they are attached form a 5 to 7 membered heterocycle containing at least one nitrogen atom, or
$XR_1$ is piperazinyl or morpholinyl.

4. A compound of formula (II)

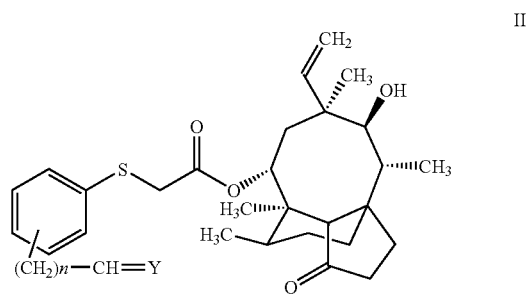

wherein
n is 0 to 5,
Y is oxygen or $NR_3$,
$R_3$ is

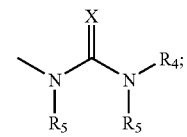

X is oxygen, sulfur, NH or $NR_7$,
or

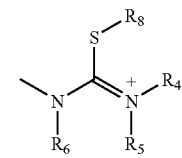

together with a corresponding anion, e.g. chloride, $R_4$, $R_5$, $R_6$, $R_7$ are hydrogen, linear or branched $C_{1-6}$alkyl or $C_{3-8}$cycloalkyl,
$R_8$ is $C_{1-4}$alkyl.

5. A compound according to claim 4, wherein Y is $NR_3$, X is $NR_7$, $R_3$ is

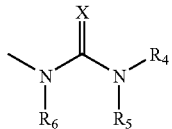

and at least one of:

$R_4$ and $R_7$ together with the nitrogen atoms to which they are attached form a 5 to 7 membered heterocyclic ring containing at least 2 nitrogen atoms, whereas $R_5$ and $R_6$ are defined as in claim 4, $R_5$ and $R_6$ together with the nitrogen atoms to which they are attached form a 5 to 7 membered heterocyclic ring containing at least 2 nitrogen atoms, whereas $R_4$ and $R_7$ are defined as in claim 4, and $R_4$ and $R_5$ together with the nitrogen atoms to which they are attached form a 5 to 7 membered heterocyclic ring containing one or more nitrogen atoms, whereas $R_6$ and $R_7$ are defined as in claim 4.

6. A compound according to claim 5, wherein Y is $NR_3$, X is $NR_7$, $R_3$ is

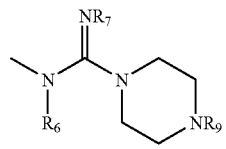

$R_9$ is hydrogen, linear or branched $C_{1-6}$ alkyl or acyl, e.g. $C_{1-6}$ acyl.

7. A compound according to claim 3, wherein said $(CH_2)_n$-group is in meta position in relation to the sulphur bound to the phenyl-ring.

8. A compound according to claim 3, wherein said $(CH_2)_n$-group is in ortho position in relation to the sulphur bound to the phenyl-ring, with the proviso that the phenyl-ring is further substituted by up to four groups independently selected from halogen, $(C_{1-6})$alkyl, aryl, aryl$(C_{1-6})$-alkyl, $(C_{1-6})$ alkoxy, $(C_{1-6})$alkoxy$(C_{1-6})$alkyl, halo$(C_{1-6})$alkyl, aryl $(C_{1-6})$ alkoxy, hydroxy, nitro, cyano, azido, acyloxy, carbamoyl, mono- or di-N—$(C_{1-6})$alkylcarbamoyl, $(C_{1-6})$-alkoxycarbonyl, aryloxycarbonyl, ureido, guanidino, $(C_{1-6})$alkylguanidino, amidino, $(C_{1-6})$ alkylamidino, sulphonylamino, aminosulphonyl, $(C_{1-6})$ alkylthio, $(C_{1-6})$-alkylsulphinyl, $(C_{1-6})$ alkylsulphonyl, heterocyclyl, heteroaryl, heterocyclyl$(C_{1-6})$ alkyl and heteroaryl$(C_{1-6})$alkyl, or two adjacent ring carbon atoms may be linked by a $(C_{3-5})$ alkylene chain, to form a carbocyclic ring.

9. A compound selected from the group consisting of

14-O-[(3-Hydroxymethyl-phenylsulfanyl)-acetyl]-mutilin,

14-O-{[3-(Aminoimino-methyl)-hydrazonomethyl-phenylsulfanyl]-acetyl}-mutilin,

14-O-[{3-[((1-Piperazinoiminomethyl)-methylhydrazono)-methyl]-phenylsulfanyl}-acetyl]-mutilin, 14-O-[{3-[(3-Ethyl-(2-ethylimino)-imidazolidin-1-ylimino)-methyl]-phenylsulfanyl}-acetyl]-mutilin, 14-O-[{3-[(1-Piperazinoiminomethyl)-hydrazonomethyl]-phenylsulfanyl}-acetyl]-mutilin, 14-O-[{3-[(2-Morpholin-4-yl-ethoxyimino)-methyl]-phenylsulfanyl}-acetyl]-mutilin, 14-O-[3-{[(2-Pyrrolidin-1-yl-ethoxyimino)-methyl]-phenylsulfanyl}-acetyl]-mutilin, 14-O-[(3-Aminomethyl-phenylsulfanyl)-acetyl]-mutilin, 14-O-[(3-Allylaminomethyl-phenylsulfanyl)-acetyl]-mutilin, 14-O-[3-{[(Furan-2-ylmethyl)-amino]-methyl}-phanylsulfanyl-acetyl]-mutilin and 14-O-[(3-Cyclopropylaminomethyl-phenylsulfanyl)-acetyl]-mutilin.

10. A compound of claim 1, wherein the compound is in the form of a salt.

11. A compound of claim 1, wherein the compound is configured for pharmaceutical administration.

12. A method of treatment of acne mediated by microbes which comprises administering to a subject in need of such treatment an effective amount of a compound of claim 1.

13. A pharmaceutical composition comprising a compound of claim 1, in association with at least one pharmaceutical excipient.

\* \* \* \* \*